(12) United States Patent
Westmeyer et al.

(10) Patent No.: US 8,820,303 B2
(45) Date of Patent: Sep. 2, 2014

(54) ACCELERATION OF A MASS BY A STRUCTURE UNDER CENTRAL OR GYRATION INDUCED FORCES

(76) Inventors: Paul Westmeyer, Woodbridge, VA (US); Renee Mazaheri, Woodbridge, VA (US)

(*) Notice: Subject to any disclaimer, the term of this patent is extended or adjusted under 35 U.S.C. 154(b) by 193 days.

(21) Appl. No.: 13/609,358

(22) Filed: Sep. 11, 2012

(65) Prior Publication Data

US 2013/0104864 A1 May 2, 2013

Related U.S. Application Data

(60) Provisional application No. 61/628,590, filed on Nov. 2, 2011.

(51) Int. Cl.
*F41B 3/04* (2006.01)
*A63B 21/06* (2006.01)
*H02G 1/06* (2006.01)

(52) U.S. Cl.
CPC .. *F41B 3/04* (2013.01); *H02G 1/06* (2013.01); *A63B 21/0608* (2013.01)
USPC .................................... 124/6; 124/1

(58) Field of Classification Search
USPC ............................................ 124/1, 3, 4, 6, 81
See application file for complete search history.

(56) References Cited

U.S. PATENT DOCUMENTS

| 5,857,451 | A | * | 1/1999 | Ciluffo et al. | 124/6 |
| 5,950,608 | A | * | 9/1999 | Tidman | 124/6 |
| 6,520,169 | B1 | * | 2/2003 | St. George | 124/6 |
| 6,712,055 | B1 | * | 3/2004 | Tidman | 124/6 |
| 7,032,584 | B2 | * | 4/2006 | Tidman et al. | 124/6 |
| 7,497,211 | B2 | * | 3/2009 | St. George | 124/6 |
| 7,500,477 | B2 | | 3/2009 | Westmeyer et al. | |
| 7,950,379 | B2 | * | 5/2011 | Tidman | 124/6 |

* cited by examiner

*Primary Examiner* — John Ricci
(74) *Attorney, Agent, or Firm* — Emch, Schaffer, Schaub & Porcello Co., L.P.A.

(57) ABSTRACT

Gyration induced acceleration of a mass is modified by inserting changes in the pathway of a mass under the influence of gyration force resulting in an acceleration to re-phase after the phase disruption.

52 Claims, 36 Drawing Sheets

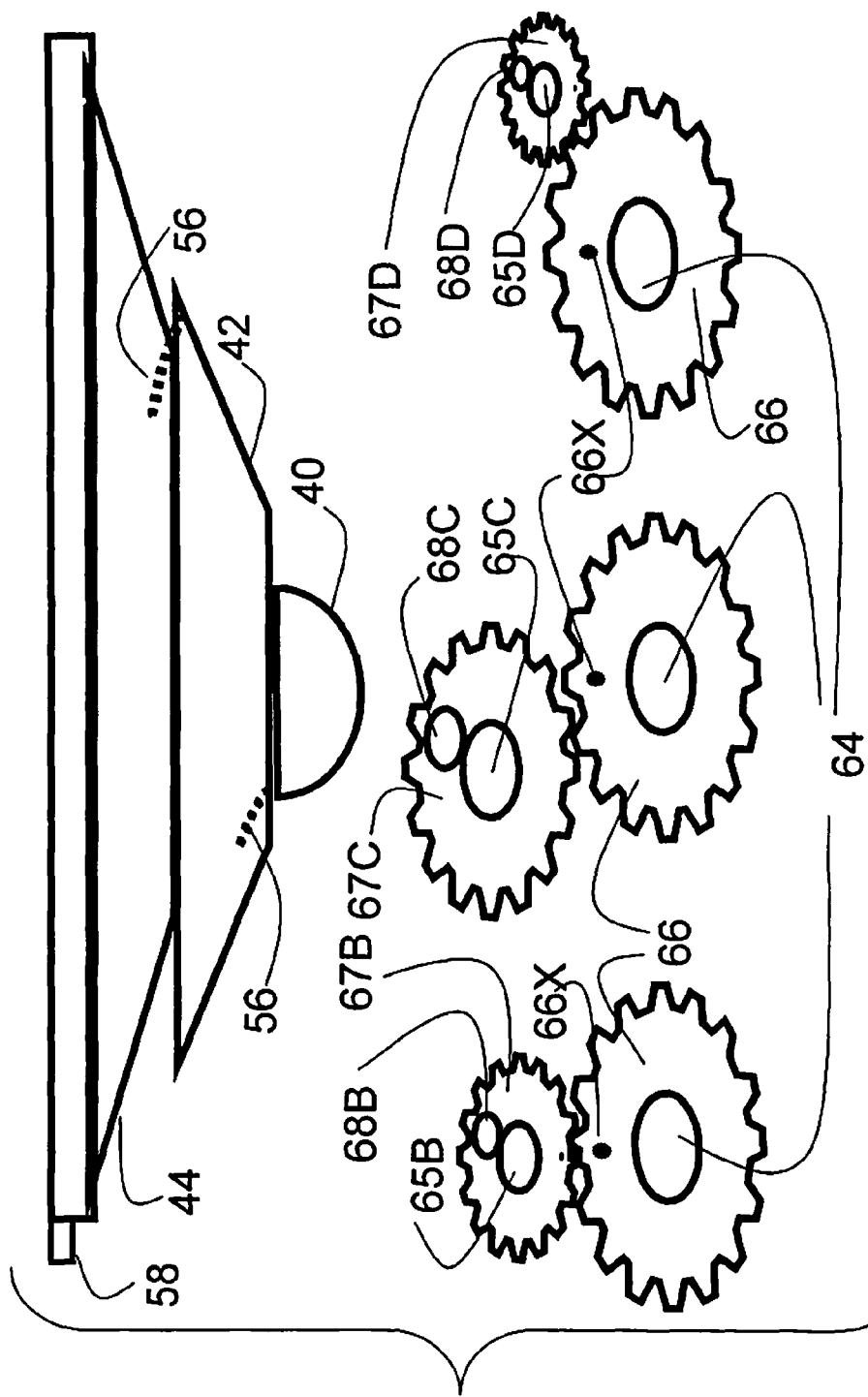

Figure 1:
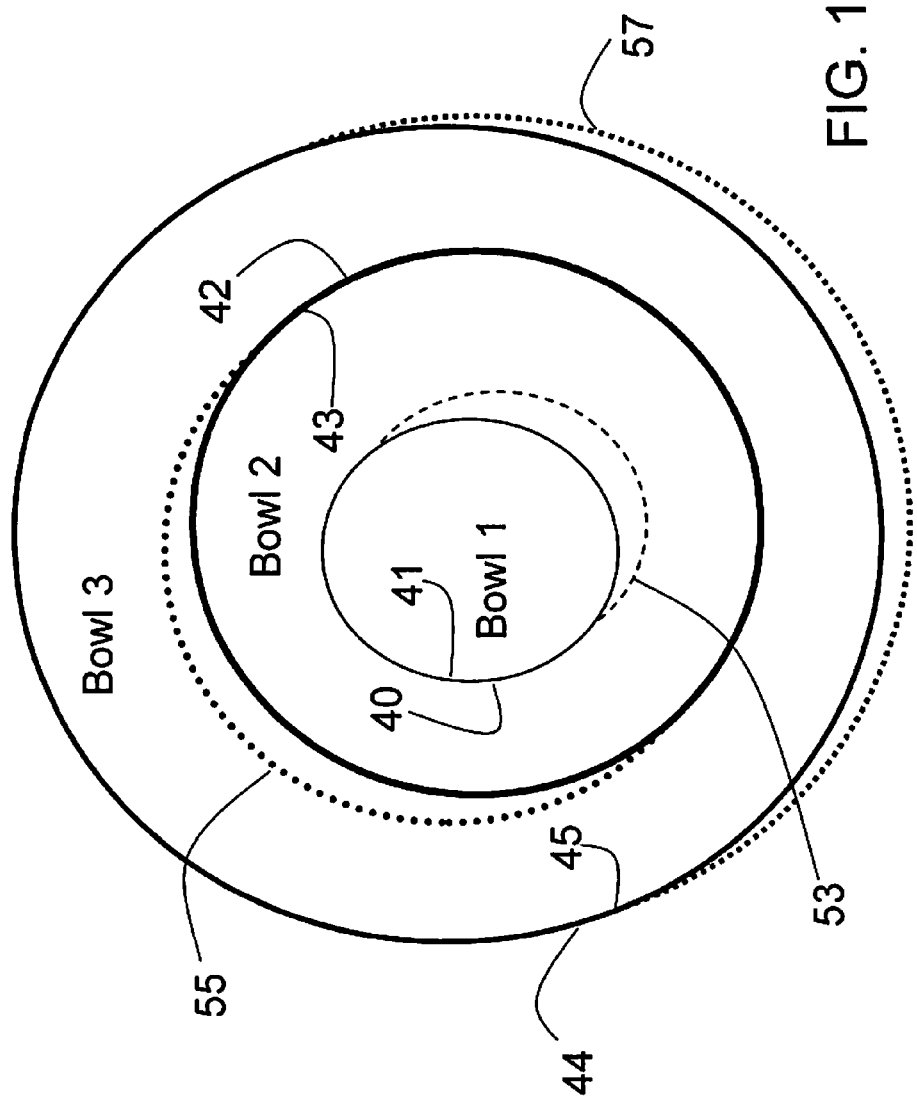

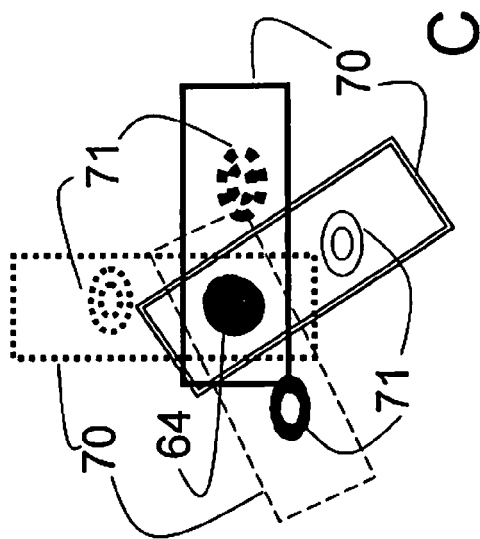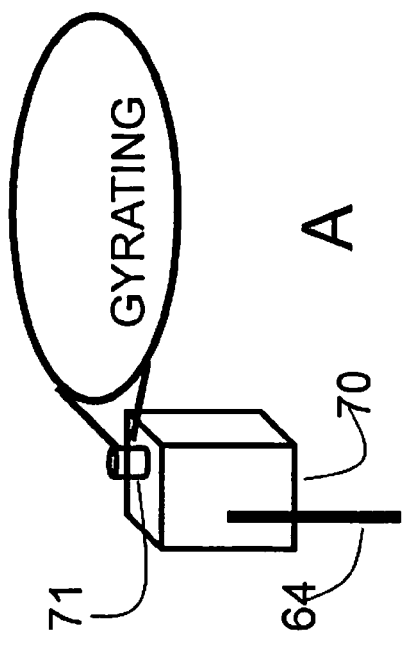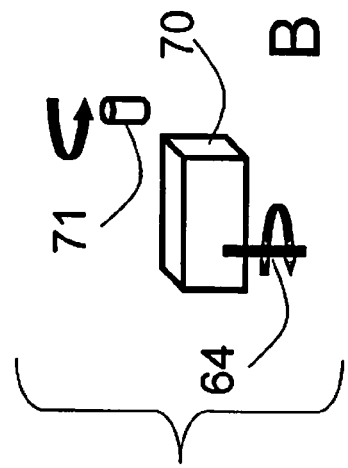
FIG. 9E

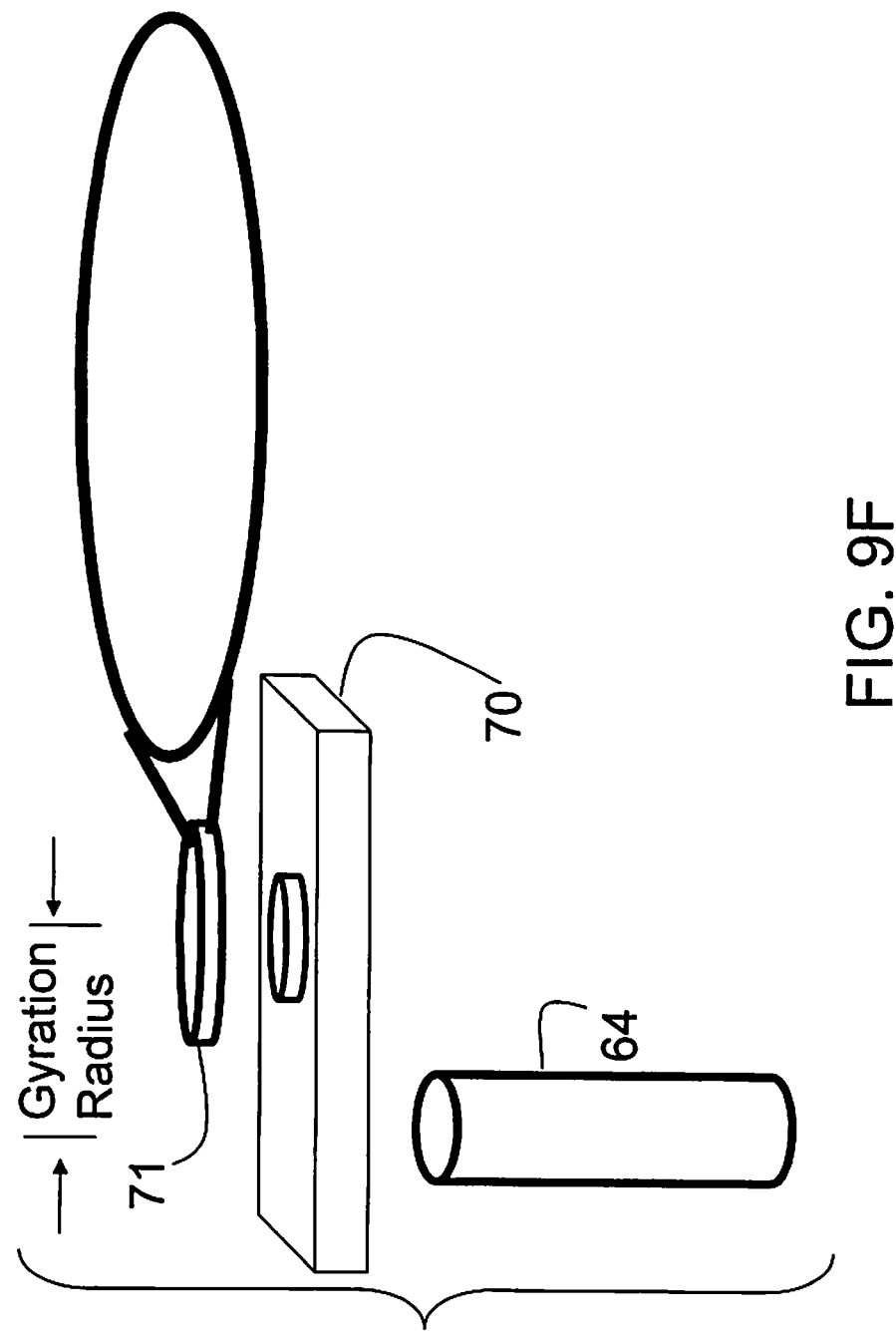

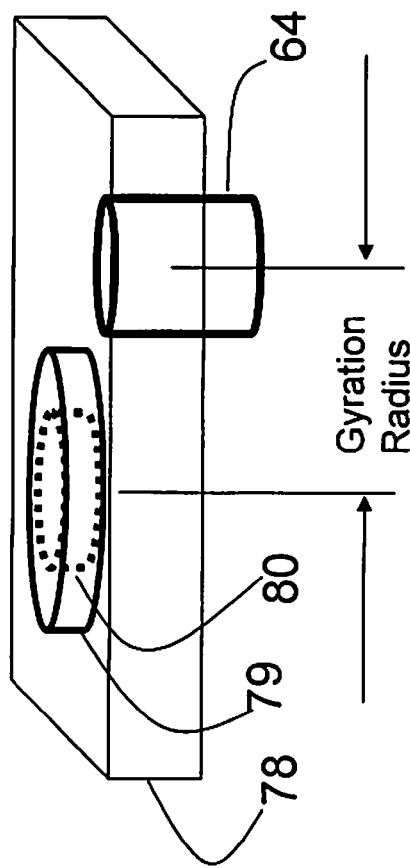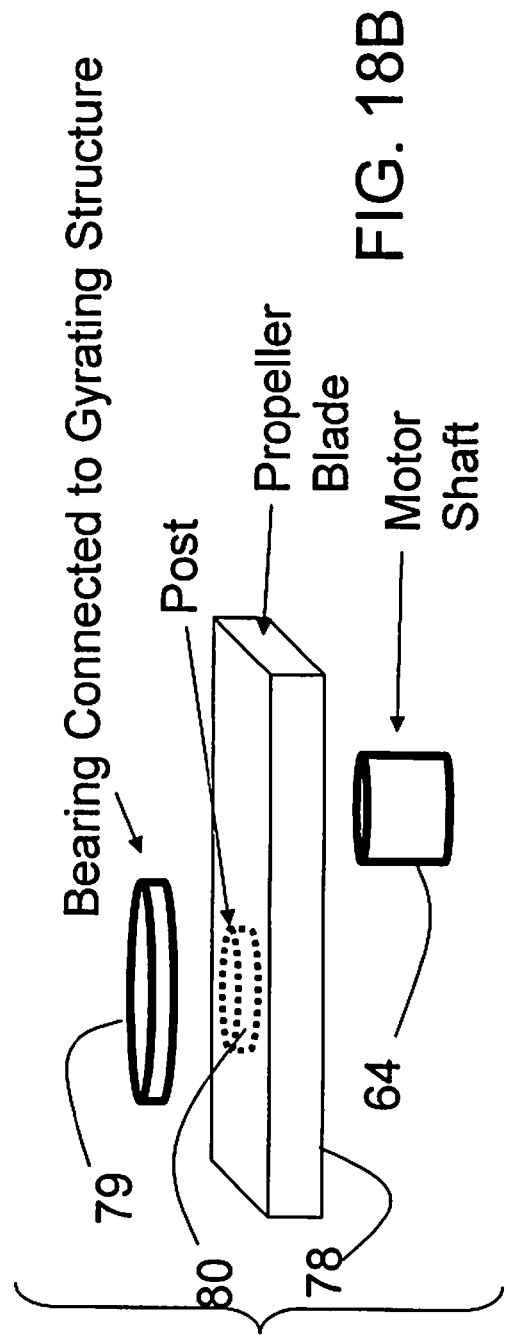

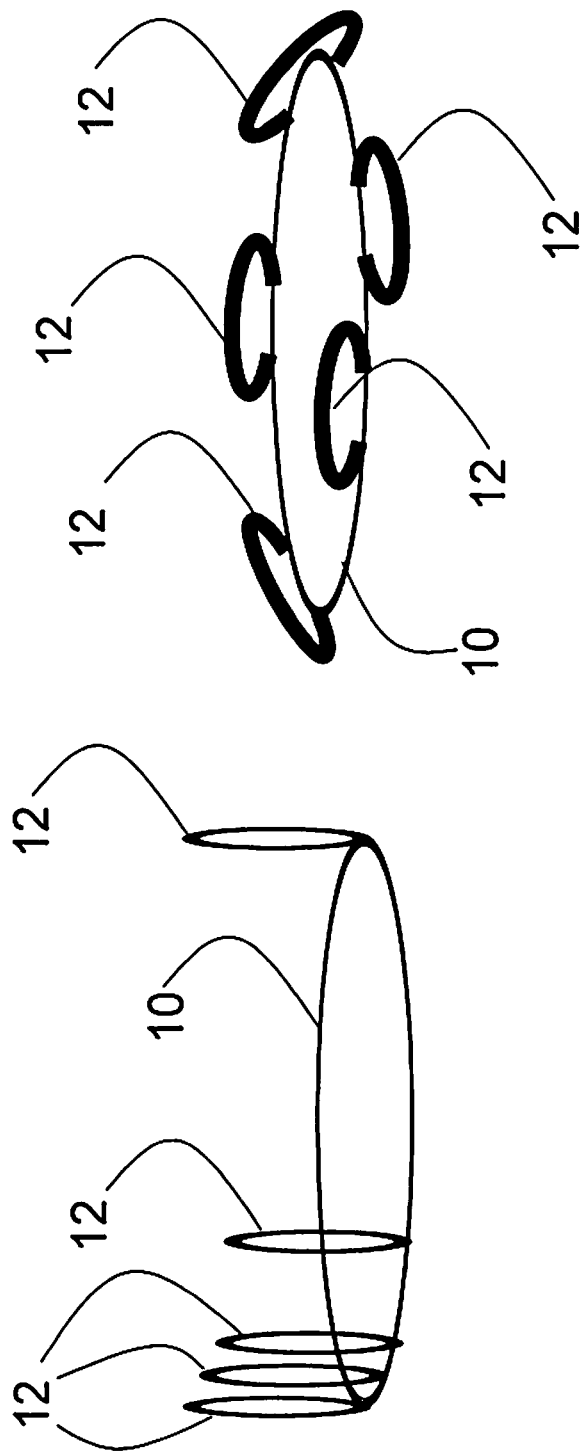

ACCELERATION OF A MASS BY A STRUCTURE UNDER CENTRAL OR GYRATION INDUCED FORCES

CROSS REFERENCE TO RELATED APPLICATION

This application is based upon and claims the benefit of U.S. Provisional Patent Application No. 61/628,590 filed Nov. 2, 2011.

BACKGROUND OF THE INVENTION

Mass subjected to a radial force will accelerate. Rotations and gyrations are two techniques to induce radial force. Gyration induced acceleration of a mass by a structure moving in a gyration mode is well understood; water inside a Hula Hoop is an example of a mass accelerated by the hoop structure which in turn is driven by a child's gyrating body. See for example U.S. Pat. No. 5,699,779. Simplified equations of motion for the mass reduce to a phase lock solution if initial conditions are satisfied. Satisfying the Hula-Hoop initial conditions to phase lock the water to the structure involves a ramping up in gyration frequency and gyration radius for the Hula Hoop. More complex mathematical equations include friction and drag, and produce a motion for the mass that is "approximately" phase locked with a slight oscillatory motion (small acceleration and small de-acceleration). Deliberately exaggerating this oscillatory behavior by means other than friction and drag is possible; mismatch of the velocity is an obvious example. A simple example is demonstrated by inserting a ball bearing into a gyrating system with different insertion velocities, the gyrating system either increases the ball's velocity or decreases the ball's velocity to phase lock it to the moving structure. These accelerations (changes in velocity) can be exploited in numerous ways.

Other gyration systems use a fixed pathway length, a fixed radius of gyration, or fixed gyration frequency, or the combination, resulting in a limited range of performance and highly restrictive initial conditions for phase stabilized acceleration.

In any phase-locked system the perfect analytical solution allows for "corrections" if the stable condition is slightly disturbed. The range of angular offset, generated by position shifts caused by routing changes, for which a stable condition can be recovered reflects into the region of pathway adjustments that will be the focus of this application.

SUMMARY OF THE INVENTION

The present invention includes methods of altering the pathway of a mass (projectile) within a phase locking gyration system. In a classic phase lock approach, once the lock is achieved continued repeats of the gyration cycle does nothing to change the velocity of the mass. By deliberately increasing the path length the mass becomes slightly destabilized because the forces are no longer in balance. Alternatively, the destabilization can be accomplished by jumping a gap and entering into a system where the phase is offset from the mass being accelerated. Once a gap is jumped, the other key parameters of a gyration system can be reset; such parameters including gyration frequency, gyration radius, and pathway length, such resets gaining performance improvements above and beyond the simple phase adjustment.

Modification of the pathway can be a delay length (aka a loop) to adjust the phase relationship between the mass and the machinery accelerating the mass. More complex modifications include delay lengths and discontinuities, where the latter is a physical gap beyond which the gyration parameters of gyration frequency, radius of gyration, overall effective path length, and phasing of mass to the gyrating force are rearranged. Benefits from these pathway changes include smaller overall packaging, a decrease in overall system power required, and less system mass, when compared to similar mass performance by previous art moving a mass to the same final velocity. These pathway modifications, combined with features of the inventors' prior U.S. Pat. No. 7,500,477, extend the usefulness of gyration induced mass acceleration.

The present invention includes two ways to alter the pathway of a mass to create re-phasing conditions leading to acceleration of a mass under a gyration forcing function. The first way to re-phase is by altering actual pathway length; a delay length or delay loop. The second is the absence of a pathway—a physical disruption in the pathway; a discontinuity or gap. These pathway changes are designed to destabilize the phasing between the mass and the structure, resulting in repositioning to take advantage of the variations in the forcing function. Disruption of the pathway, such as by a physical discontinuity, changes the phasing and allows for changes in the frequency of gyration, the radius of gyration, and overall pathway length, after the mass is "re-acquired" to a different pathway beyond the gap.

Discontinuity gaps produce significant consequences by resetting the gyrating system's base parameters: gyration frequency, gyration radius, and overall pathway length. These are in addition to the phase parameter mentioned in the previous paragraph.

When multiple discontinuity gaps are used there can be a combination of values for each parameter; for example, the gyration radius may be increased then decreased or vice versa, or even increased then decreased then increased again.

The reset potential of these four system parameters (phase, gyration frequency, gyration radius, and path length) within a single system is not demonstrated by the prior art.

For the Hula Hoop the overall path length is fixed, and the gyration frequency and radius are defined by the human operating the toy. Other prior art, as exemplified by Tidman U.S. Pat. No. 6,014,964, offers a variety of fixed gyration frequency and gyration radius systems, except one which is a closed system that doesn't allow the mass to exit the system (not very useful). The prior art systems have constrained initial conditions and are continuous two dimensional pathways. Lacking use of the third dimension is problematic for practical usage where packaging, maintainability, and system reliability are serious concerns.

Delay Lengths for Phasing Reset:

Conceptually the delay length could be done by taking a conventional Hula Hoop and adding a small loop perpendicular to the plane of the main Hula Hoop. Any fluid within the tube that is phase locked with the hips of the human powering the Hula Hoop would become unlocked upon entry into the small perpendicular loop. Water reinstated into the main Hula Hoop after its excursion through the perpendicular delay loop is no longer phase locked. Under some conditions (human variability will determine if the conditions are satisfied) the phase offset will result in the water being accelerated to a higher than phase locked velocity (an overshoot). That very uneven acceleration profile will induce a small overshoot which will be dampened until phase lock status is regained. An interesting new toy idea would be to create a new version of the hula-hoop where several internal conduits (aka multiple pathways) with several delay loops on each internal conduit are used to re-phase the working fluid.

Planning these overshoots can be done such that increments of velocity are added before phase lock is reestablished. For an open ended system the mass can exit before the dampening reduces the added velocity.

There are two ways to 'define the actual length' for a delay length, recognizing the purpose is to shift the media into a different phase relationship with the gyrating structure.

The first method assumes all phases' angle change is accounted for in delay pathway length and the media's exit and re-entry into the gyrating structure(s) are the same tangential intersection. The angle of phase change is converted to an equivalent time duration at that gyration frequency, and that time duration is computed as physical length at the velocity the media is traveling when exiting the gyrating structure. For example, if the gyration frequency is 8 Hz, and a phase delay of 80 degrees is desired, then $^{80}/_{360}{}^{th}$ of 125 milliseconds (8 Hz) is the time the media is required to stay outside the gyrating system in the delay pathway, approximately 28 milliseconds. If at the time of exit from the gyrating system the media has a velocity of 18 meters per second then the delay length needs to be about 50 centimeters, as a 360 degree loop perpendicular to the plane of the gyrating structure; the loop is about 8 centimeter is radius.

The second method uses a smaller delay pathway length and a repositioning of the re-entry back into the gyrating system which is not the same tangential intersection with the exit from the gyrating system. Using the same 8 Hz, 80 degrees of phase shift and 18 m/s velocity, if a 4 centimeter radius delay loop is inserted the time the media is in the delay loop is approximately 14 milliseconds. In 14 milliseconds the gyrating system has advanced only 40 degrees (relative to the point where the media exited the gyrating system). To account for the other 40 degrees the Delay Length is reconnected to the gyrating structure at a point that is 40 degrees "behind" the delay length exit feeding the delay length (this is obviously not a 360 degree loop.)

Discontinuities for Phasing Reset:

A similar effect, getting into the sweet spot of the acceleration profile, is accomplished by a gap that allows the mass to exit one phase relationship with the structure and enter another phase relationship. The classic gyrating bowl with a ball bearing rolling inside is used to define a simple single gap system. As the ball bearing reaches phase stability it is forced into a discontinuity. One way to build in a discontinuity is to have the bowl just a bit too small to establish phase lock for a given gyration frequency and gyration radius; thus, the ball bearing will escape; it jumps a gap into a second bowl. This second bowl, with identical gyration radius and gyration frequency, can add velocity if the phase is properly offset from the first bowl's phase. If the bowls are in an identical state of "phase" the ball bearing's time to travel will introduce a phase shift of the bearing relative to the second bowl, since the ball bearing is not under a force induced by gyration while in the delay length or gap. Because the two bowls are independent structures they have the potential for different gyration frequency, gyration radius, phase, and absolute size (pathway length). None, or all, or some of these parameters can be different for bowl two as compared to bowl one.

Much of the structures of the second and any subsequent bowls in this example are unnecessary because the ball bearing is only phase stable near the maximum radius. The second and subsequent bowls are replaced with annular rings, less mass than the bowls they replaced, which translates into a power savings for the system. To prevent these objects (bowl and annular rings) from impacting each other, the selections of dimensions and shapes, and full range of motions must be considered. A true dynamic envelope is maintained for each bowl/annular ring in the series. One special case for this process is a series of harmonic gyration frequencies; these harmonics can be deliberately phased (much like clocking a geared system) to enable absolute control over the phase relationship of the mass to the accelerating system. Non-harmonic gyration frequency systems will have more complex relationships.

Active controls on the dynamic envelope can be accomplished by sensors monitoring each component in combination with any number of techniques for speed controls on the power systems (such as variable speed motors with feedback controls). Without active controls the full uncontrolled dynamic envelope must therefore be understood to prevent mechanical interferences. One benefit of active controls is to reduce and to accommodate the dynamic envelope uncertainties. Active controls can be used to control the velocity and position of any media.

A conceptualization for such a system is a bowl operating at a frequency and a series of annular rings at higher frequencies. Between the bowl and the first annular ring is a shaped trap (delay length or gap construct) that is rigidly attached to either the bowl or the annular ring, but not both, or not attached to either the bowl or annular ring. Similarly shaped traps are used to move the media from one annular ring to the next. Since the bowl and rings are gyrating at different frequencies and potentially with different gyration radii, and can use delay lengths within their structures, the possible combinations and permutations is extensive.

Yet another conceptualization would be to have a shaped trap that is attached at both ends. A telescoping flexure is connected to the hard attach points which moves with respect to both hard attach points but is constrained to not detach from either hard attach point, thus permitting different values for any or all the parameters. This design approach is the logical decoupling of gyration into a pair of perpendicular axes, where one axis is the telescope and the other is the flexure motion.

A third concept is a 'service loop' of pathway in a coil-shape that is free to flex as needed to absorb the energy imparted onto the service loop from the gyrating structures it is attached to.

Service loops can be added to either a shaped trap or a telescoping flexure device.

Lastly, a shaped trap can have no moving parts, but sufficient overlap (more than twice the gyration radius) which each moving structure (with one or more arcuate surfaces) to prevent the media from exiting the structures until the end of the pathway.

All of these configurations have been described as static routes, i.e. no active switching devices. It is very practical to insert motion sensitive switches that either open or close a portal in response to the same forces that accelerate the mass. Active devices can be as simple as springs, or electro-mechanical devices triggered by the forces themselves, or sensor driven devices. Generally speaking these switching frequencies are less than 100 to 200 Hertz.

The exit characteristics of the mass are velocity and angular dispersion. Mass exiting a gyrating machine can be used to perform a number of purposes such as abrasion, cutting, boring, etc. . . . If a smaller angular dispersion is required then the final stage of acceleration should be done with a small radius of gyration, unless a separate angular reduction device such as a telescoping flexure is used. On the other hand if a large dispersion is required then a large radius of gyration is desired for the last stage.

Once outside the gyrating structures the media can be routed by any number of conduits. One abrasion application is to remove hardened concrete from the interior surfaces of the concrete mixer truck. Reaching all the curved surfaces will require significant angular dispersion of the media by the conduit.

As for physical sizes the smallest practical size is defined by molecular limits, which means nanometer class systems are probably not realizable but micron class could be. Upper limit on the size of a practical machine is tens of meters in diameter. At 100 meters diameter a machine would be capable of many kilometers per second of exit velocity; at these high Mach numbers the equations are far more complex because materials have different friction properties and if used in an atmospheric situation, the sonic boom issues would have structural impacts or similar problems.

IN THE DRAWINGS

FIG. 1 is a top view of bowl shaped surfaces. The whole bowl is shown for the smallest bowl and only partial bowl surfaces are shown for the larger ones.

FIG. 2 is a side view of the bowls shown in FIG. 1, namely a small bowl plus 2 larger segments showing discontinuities of the accelerating surfaces (small bowl and two larger bowl segments) that act on the media (projectile) and the dynamic motion of these structures as depicted by the dash lines.

FIG. 3 is a view similar to FIG. 2 but showing a discontinuity gap with a discontinuity trap added (side view of 3 surfaces—small bowl and 2 larger segments).

FIG. 4 shows phase shifts of the $2^{nd}$ and $3^{rd}$ surfaces relative to the small bowl (top view of 3 surfaces (bowl shapes)). Combining FIGS. 3 and 4 in a true 3-D view, the discontinuity trap between any two surfaces would have a structure to guide the projectile (media) from one surface to the next.

FIG. 5 is a side view of 3 surfaces with discontinuity traps and with an exit portal (noting phase offsets, different radius of gyration, different frequency of gyration).

FIG. 6 is a side view showing a bowl and two larger segments each in the shape of a megaphone (looks like a trapezoid in 2-dimensions) surfaces.

FIG. 7 is a view similar to FIG. 6 showing a lower bowl in combination with 2 upper bowl segments having concentric cylinders (note: discontinuities shown).

FIG. 8 is a view showing pathway trace options of the cylinders "unwrapped" with the top expanded surface having no surface features to guide a projectile (media) through the pathway and the lower expanded surface having channels for guiding the media.

FIG. 9A shows a power shaft connected to a rotating main gear driving a second rotating gear with a pin forced into gyration motion.

FIG. 9B is a view similar to FIG. 9A showing the gears rotated to a different position.

FIG. 9C is a view showing nested gyrating structures, a bowl and two trapezoids, which are gyration driven by common power plant (gears, pulleys, etc.).

FIG. 9D has a single rotating gearing system connected to a single gyrating bowl.

FIGS. 9E, 9F, and 9G show another way to generate gyrating motion for a structure attached to a rotating shaft.

FIG. 10 is a view showing a phase shifted dynamic envelope for a vertically stacked machine of several stages.

FIG. 11 is a side view showing an embodiment with a lower bowl and three trapezoid sections above. The lower bowl and topmost trapezoid are shown with their rotation-to-gyration mechanisms; all three discontinuity traps are shown.

FIG. 12 is a side view of a bowl showing transitions resulting from the 'discontinuity traps' in previous figures.

FIG. 13 defines the transition, shown from side view in FIG. 12.

FIG. 14 is an exploded view of one possible configuration, a simple vertical stack of structures using a common drive shaft axis.

FIG. 15 depicts another possible configuration with vertically offset structures.

FIG. 16A is a front view of four stage machine.

FIG. 16B is a side view of the four stage machine shown in FIG. 16A.

FIG. 17A is a schematic view showing details of one type of rotation-to-gyration mechanism.

FIG. 17B is an enlarged view of a portion of FIG. 17A.

FIGS. 18A and 18B are expanded details for the interfaces between the motor shaft and the bearing connected to the gyrating structure FIG. 19A is a perspective view showing the top of one plate of a composite of two plates.

FIG. 19B is a perspective view showing the bottom of the second plate of the composite.

FIG. 20 shows a single 'stage' gyration structure (no enclosure, no wobble control).

FIG. 21 shows three 'stages' (also no enclosure and no wobble control) without any specific arcuate surface features for channeling the media.

FIGS. 22-25 are schematic views showing various delay length designs.

FIGS. 26-29 are schematic representations with one or multiple perpendicular delay loops.

DETAILED DESCRIPTION OF THE INVENTION

Three families of preferred embodiment exist, one family is based upon just delay lengths (loops), a second family is based upon discontinuities (gaps), and a third has both features.

The Discontinuity embodiment may be represented by a series of bowl shapes. A two bowl embodiment would be a stacked larger bowl completely shadowing the smaller bowl. The smaller bowl would have a "tube-like" structure penetrating from the inner surface of the larger bowl. The ball bearing gains velocity in the smaller bowl before entering the tube structure to be transported onto the inner surface of the larger bowl. This transfer is at a low angle of attack (glancing, not bouncing off, and captured onto the inner surface of the larger bowl). The two bowls are gyrating at the different frequencies, and with different radii of gyration. The smaller bowl would have the larger radius of gyration. It is important to provide an adequate dynamic envelop so that the bowls don't ever touch as they gyrate. There is one power plant driving these two bowls.

Referring to FIGS. 1-5 there is shown three stacked bowls, a lower bowl 40 (BOWL 1) having an inner surface 41 defining a section of a sphere, a larger intermediate bowl 42 (BOWL 2) and a still larger upper bowl 44 (BOWL 3). The intermediate bowl 42 and upper bowl 44 each has an inner surface 43 and 45, respectively, defining a section of a sphere; however, their inner surfaces 43 and 45 preferably have an open bottom. Dashed line 57 reflects a second edge position for the largest bowl 44, similarly dashed line 55 reflects a second position for the intermediate sized bowl 42, and dashed line 53 reflects a second position for the smallest sized bowl 40.

As shown in FIG. 2, the bowls are aligned on a common axis A such that a first gap 48 is provided between the upper edge 50 of inner surface 41 and the inner surface 43 intermediate bowl 42 and that a second gap 52 is provided between the upper edge 54 of inner surface 43 and the inner surface 45 of the upper bowl 44.

Figure 2:
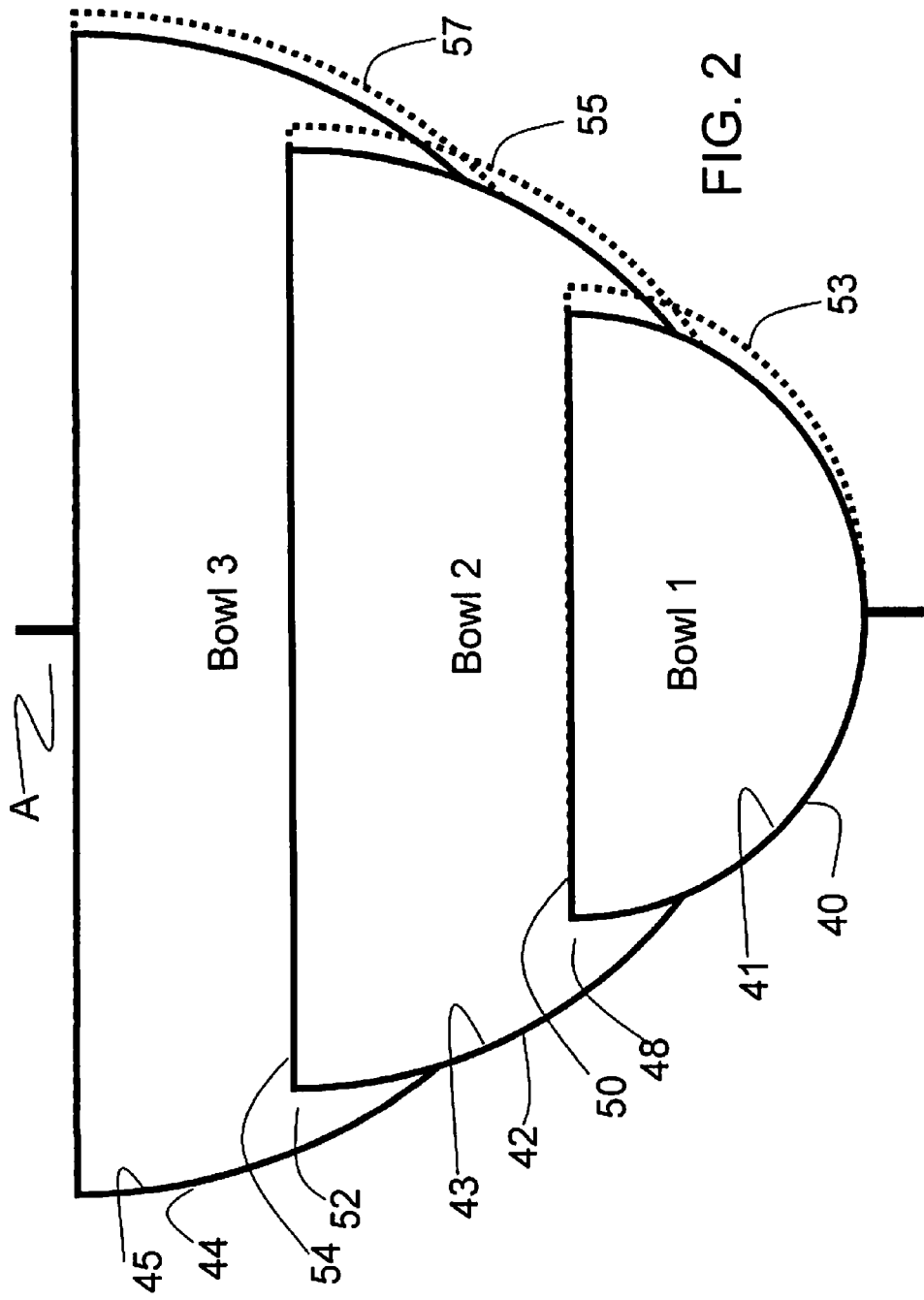

As will be appreciated, FIG. 2 shows the physical overlap between structures, thus a dynamic envelop is noted, which means the full range of motion of each bowl must be accounted for to prevent physical collisions between bowls when in motion. This dynamic envelop is required for each situation where the bowls appear to have an overlap region; the dash lines on the right sides of the bowls 40, 42, 44 and in subsequent figures represents this dynamic envelope. The dash lines 53, 55 and 57 represent the extent of movement of the respective bowls 40, 42, 44 during gyration.

Figure 3:
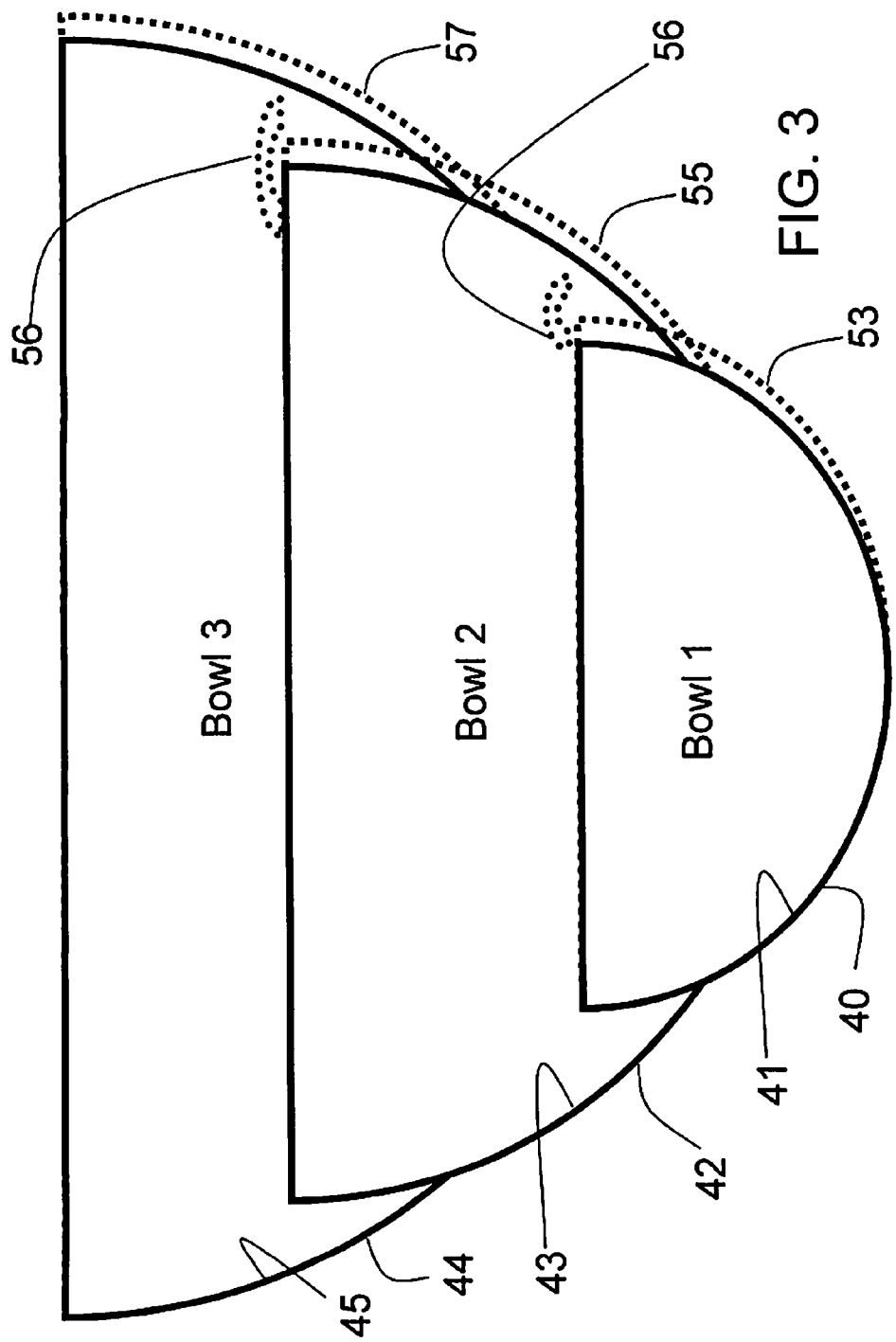

FIG. 3 shows a 'discontinuity trap 56'. The discontinuity trap 56 is a physical conduit from one gyrating structure bowl 40 to another gyrating structure bowl 42. For ease of manufacturing the discontinuity trap can be attached to either gyrating structure but not both gyrating structures unless a stress relief device is used between the attached points. These discontinuity traps 56 are shown with dash lines added to reflect their motion.

Discontinuity traps allow one or more parameters that define a gyrating structure (gyration frequency, gyration radius, gyration phase, and overall path length) to be adjusted. A discontinuity trap 56 channels the mass/media as the mass leaves the first bowl 40 and enters the second bowl 42, and likewise another trap 56 channels the mass as it leaves the second bowl 42 and enters the third bowl 44.

Figure 4:
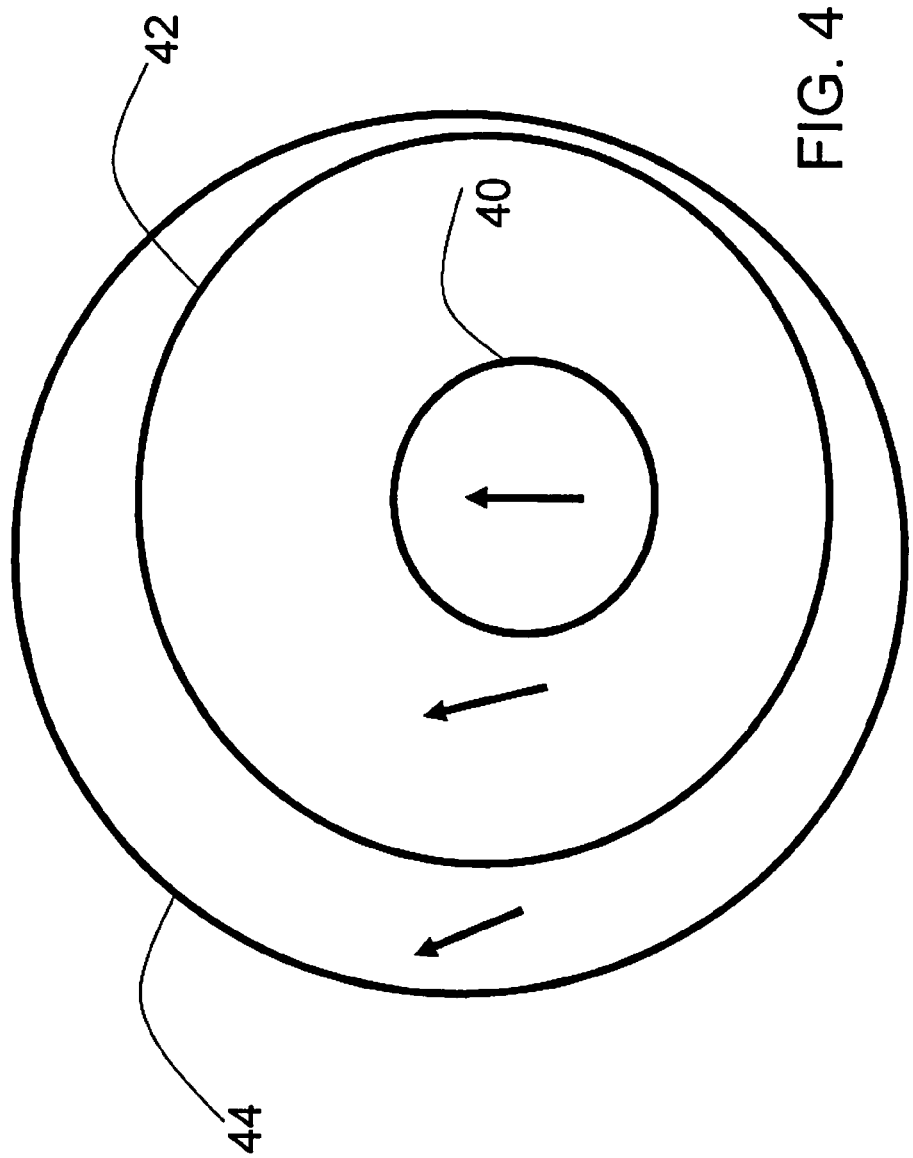

FIG. 4 shows one parameter of this system wherein the phase of each structure/bowl 40, 42, 44 as seen from above has been shifted to lie on a different axis than the adjacent bowl.

Figure 5:
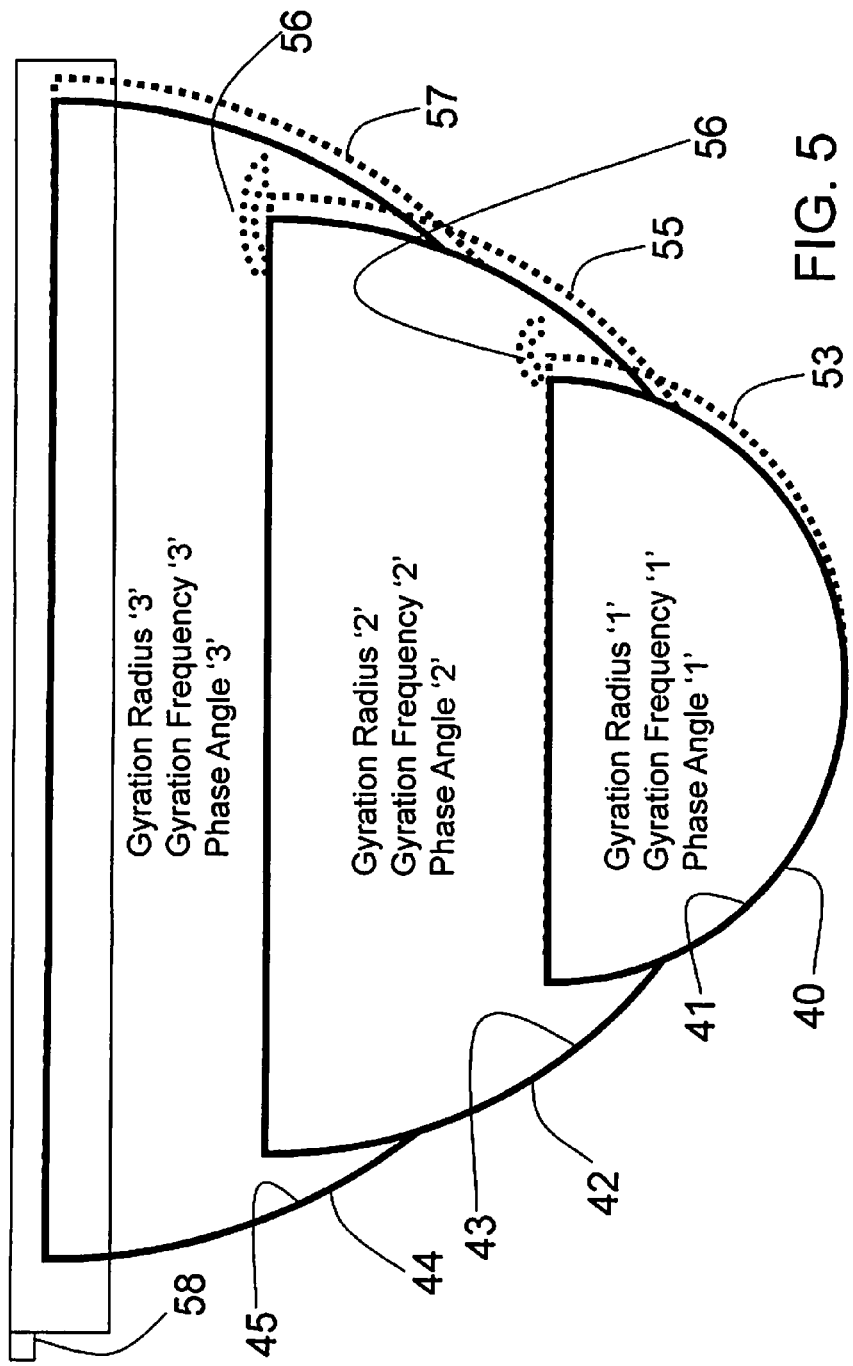

FIG. 5 shows the three bowls 40, 42 and 44 and sets out different values for the key parameters of gyration frequency, phase angle and gyration radius. An exit portal 58 is shown at the top of the upper bowl 44 as are the discontinuity traps 56.

As in the case of FIGS. 1-3, dash lines have been added to FIG. 5 to show the movement of the bowls 40, 42 and 44 as a result of the gyration.

Thus the "gap" bowl configuration of FIGS. 2, 3 and 5 uses a series of ever larger bowls with mass removed from the larger bowls 42, 44 (effectively cutting the bowls' bottom out making them annular rings). The sections of the bowls that are left are connected to individual power plant nodes, geared off the same shaft or different drive shafts and will be similar to FIGS. 9A and 9B. Nominally, the gyration frequencies are harmonics, and the radius of gyration is decreased as the diameter increases. All bowls/annular rings have "tube-like" structures to move the mass/media from one surface 41 to another surface 43 and then to another surface 45.

Figure 6:
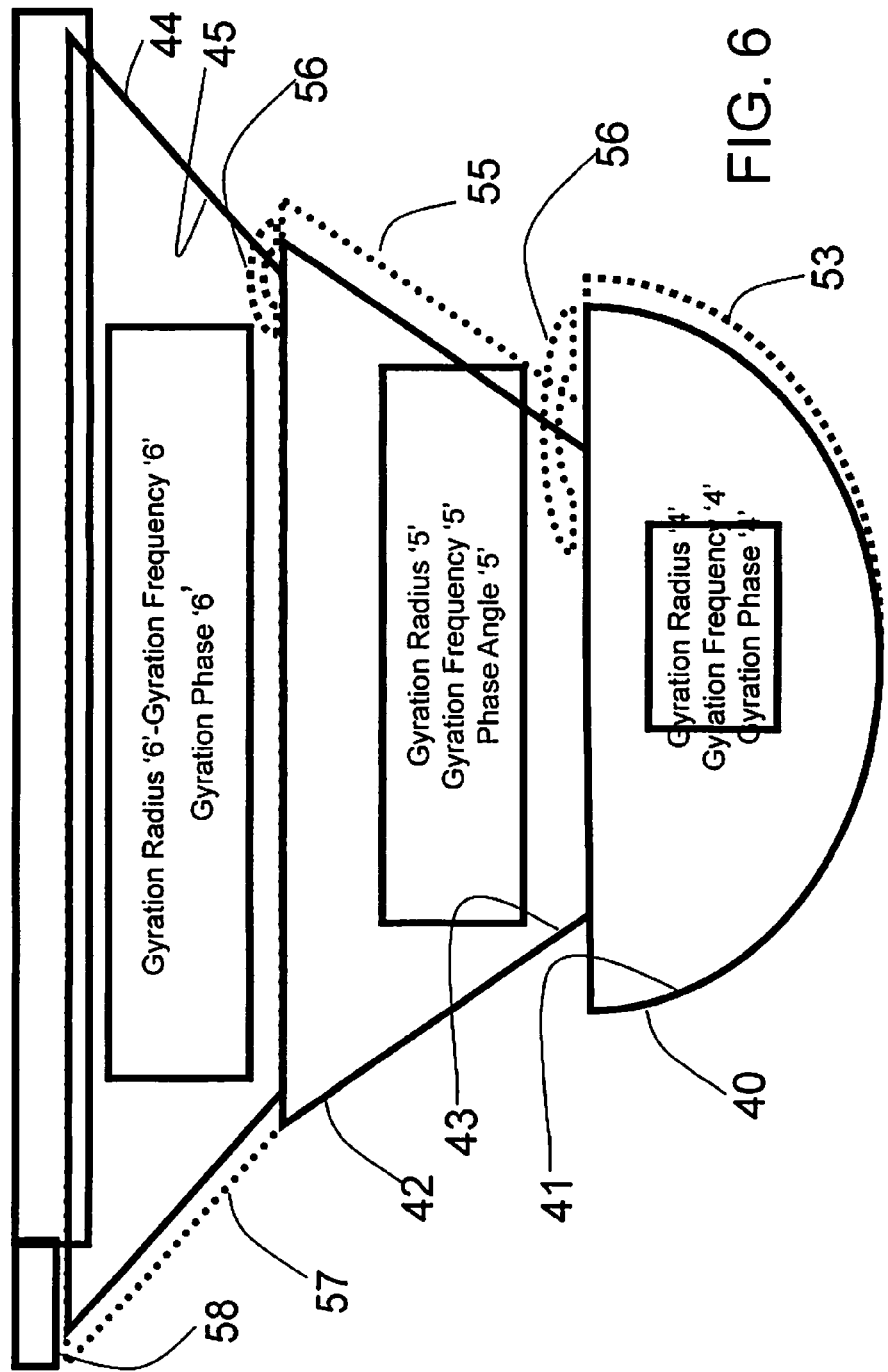

FIG. 6 shows another embodiment in which the intermediate bowl 42 and the upper bowl 44 (cone shapes rather than bowl shape) are each having a trapezoidal configuration in cross section with their respective inner surfaces 43, 45 following a straight line path. The path of the inner surfaces 43 and 45 may be at the same angle or at different angles. Discontinuity traps 56 moves the mass/media from a larger diameter inner surface 41 to a smaller diameter inner surface 43, and similarly from 43 to 45.

Figure 7:
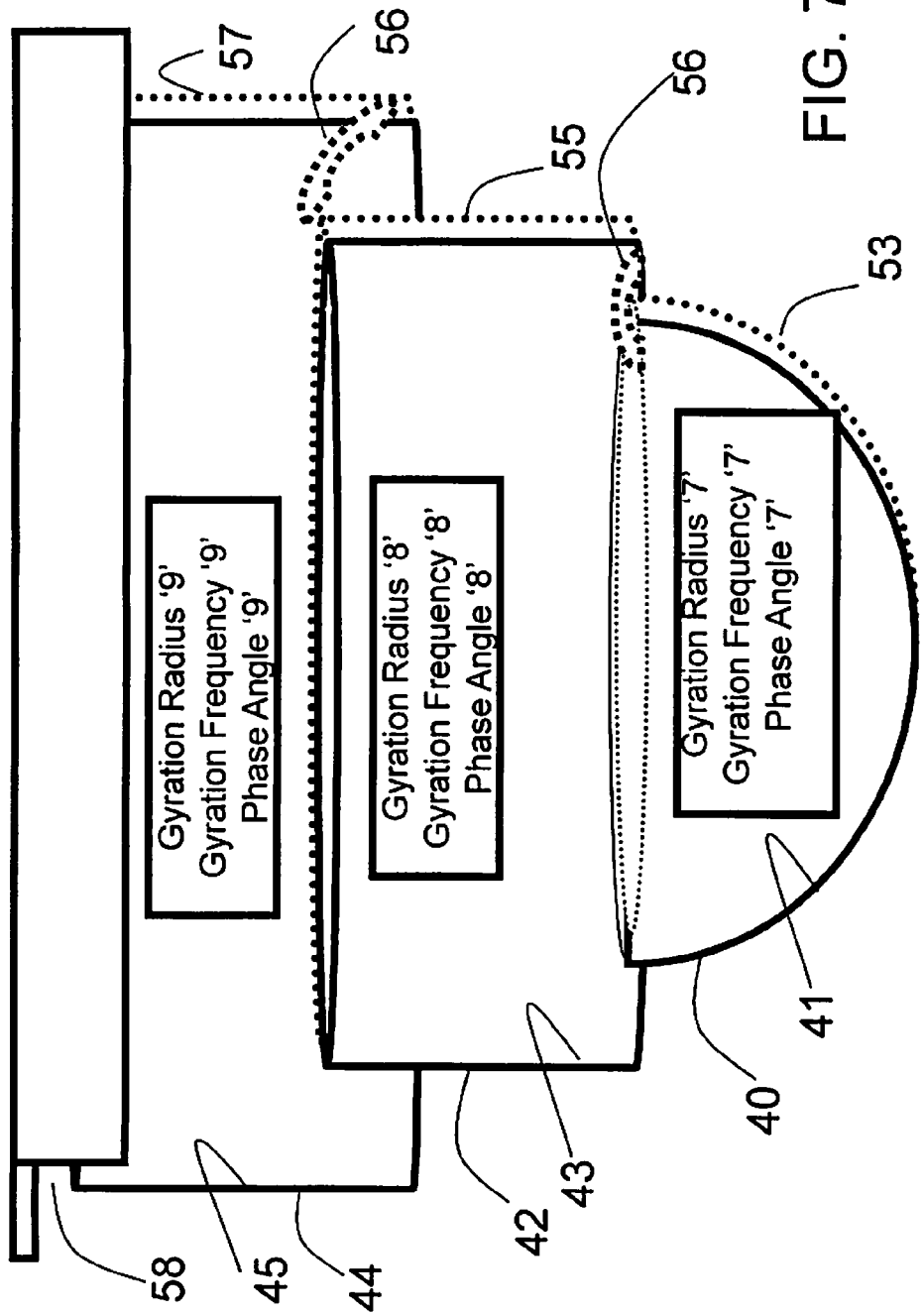

FIG. 7 is similar to FIG. 6 but shows an embodiment in which the intermediate bowl 42 and upper bowl 44 each have a cylindrical shape but of different diameters. Discontinuity traps 56 moves the mass/media from a smaller diameter inner surface 41 to a larger diameter inner surface 43, and similarly from 43 to 45.

FIGS. 6 and 7 also show the different parameters.

In FIGS. 5, 6 and 7, the added information is specific to each gyrating structure; gyration frequency, gyration radius, and phase angle.

All of these figures have discontinuity traps 56. Dash lines are shown for each structure (dynamic envelop). In each figure, except FIG. 6, the pathway length gets larger; the media (ball bearing as an example), would start in the lower bowl 40 and gain velocity unit it escapes the upper bowl 44 at the top via the exit portal 58. FIG. 6 reflects the possibility of reducing the pathway length at a discontinuity trap.

The exit portal 58 will be the point in the structure where the media departs, no longer under the accelerating influence of the gyrating parts.

In FIGS. 6 and 7 the form factors may be critical to the effectiveness of the structure. The form factors of FIG. 7 with concentric intermediate and upper bowls 42, 44 allows for more compact designs since physical interferences are easy to control. This is especially useful for "nesting" where phase shifting effects are being maximized.

Figure 8:
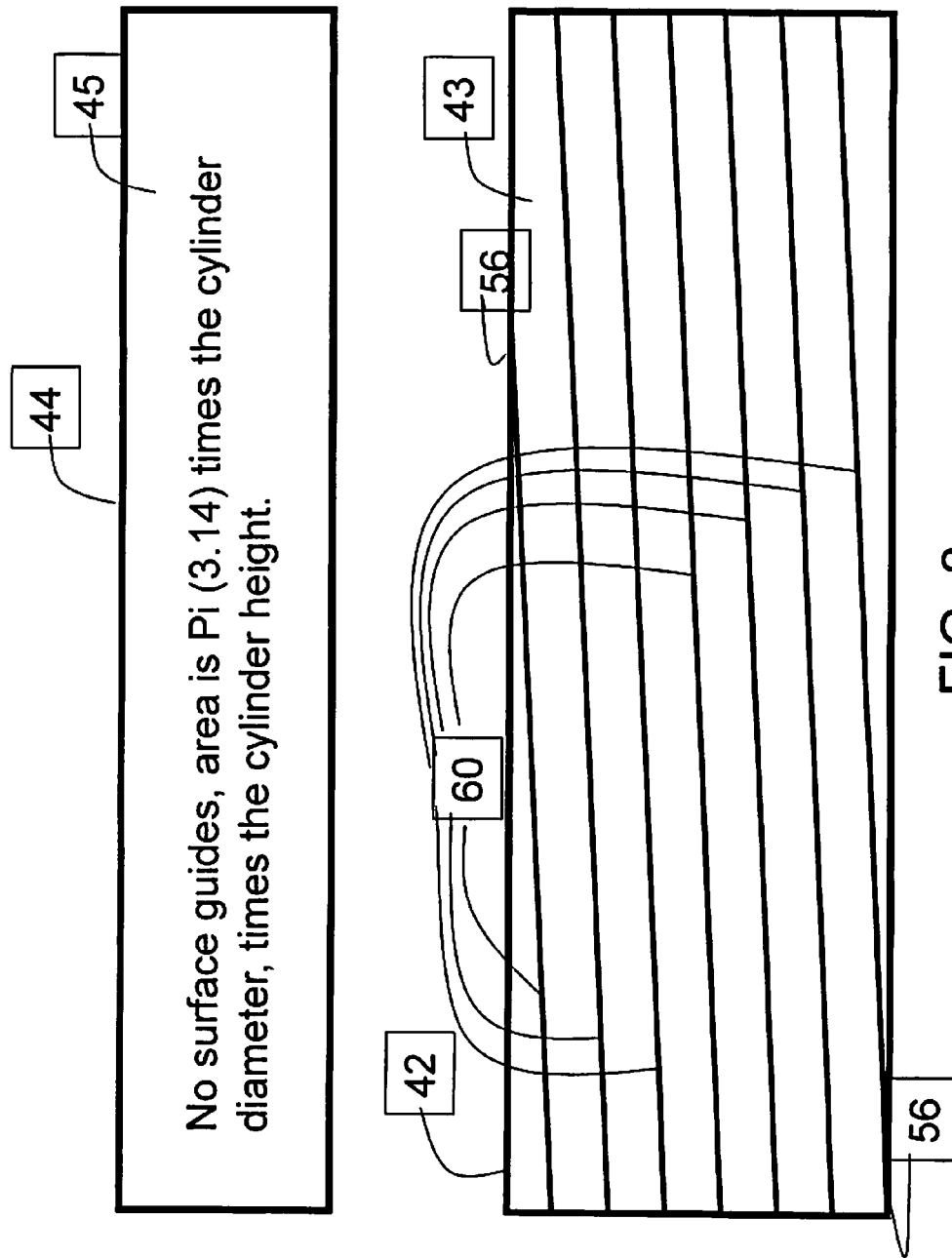

In FIG. 8 the upper bowl 44 and intermediate bowl 42 of FIG. 7 are shown unwrapped looking at their respective inner surfaces 45 and 43. Inner surface 43 has channels 60 forming recessed paths in which the media M moves. Thus, the channels 60 guide the travel of the media. Channels 60 of different sizes may be enveloped at the same time within the bowl 42 thereby accommodating different size media with different entrances and exit portals.

The inner surface 45 of the upper bowl does not have channels but rather is smooth. The smooth inner surface 45 allows the media to take any pathway consistent with the forces. In contrast, the channeled pathway 60 constrains the media. In either case the media is limited in its exit from the surface by either the discontinuity trap (the discontinuity traps have been shown in 'cut away' only but they are around the full circumference of the gyrating structure) or the exit 'lid' (which covers the entire circumference). If desired, delay loops may be inserted in the channels 60.

Figure 9A:
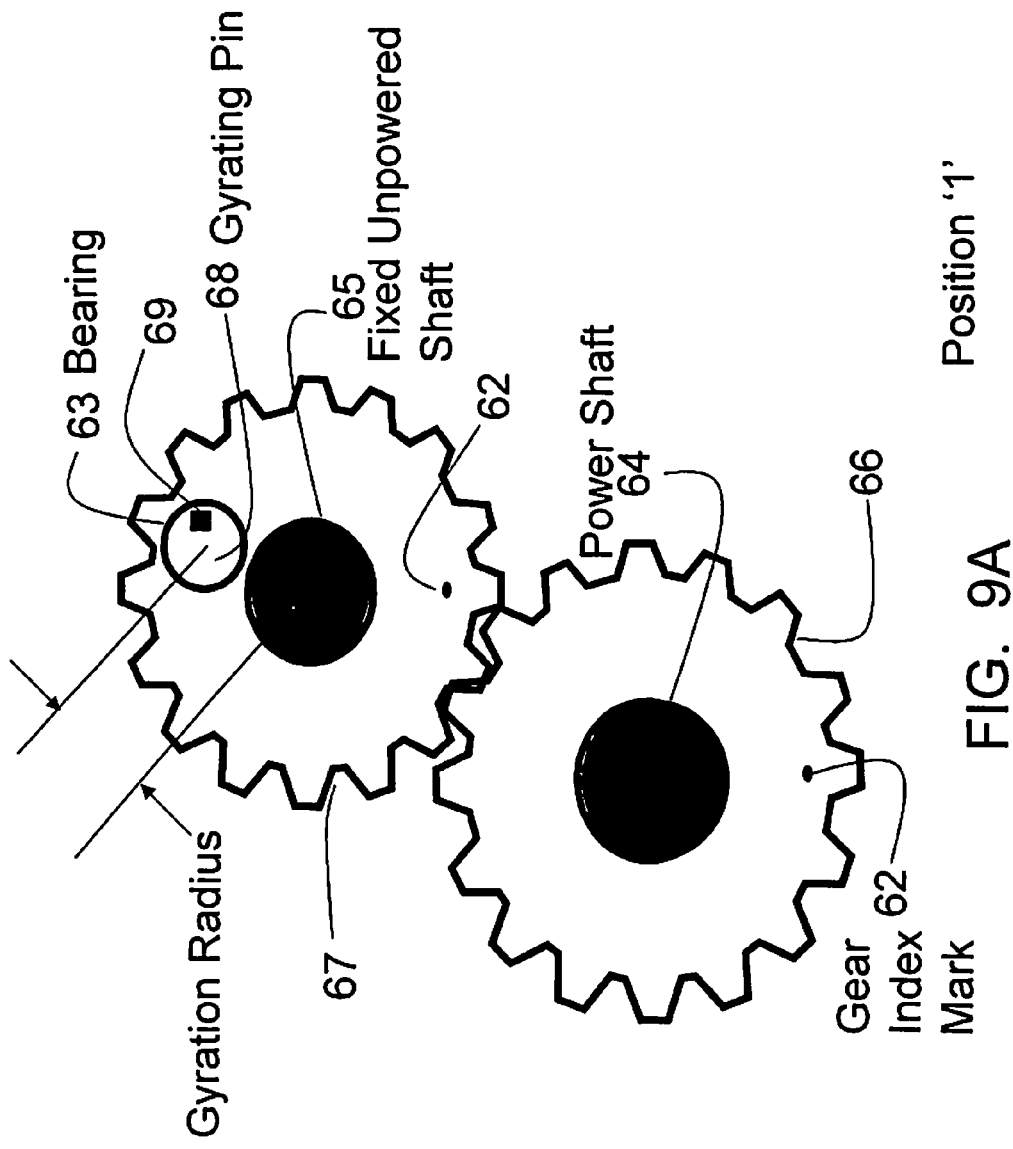
Figure 9B:
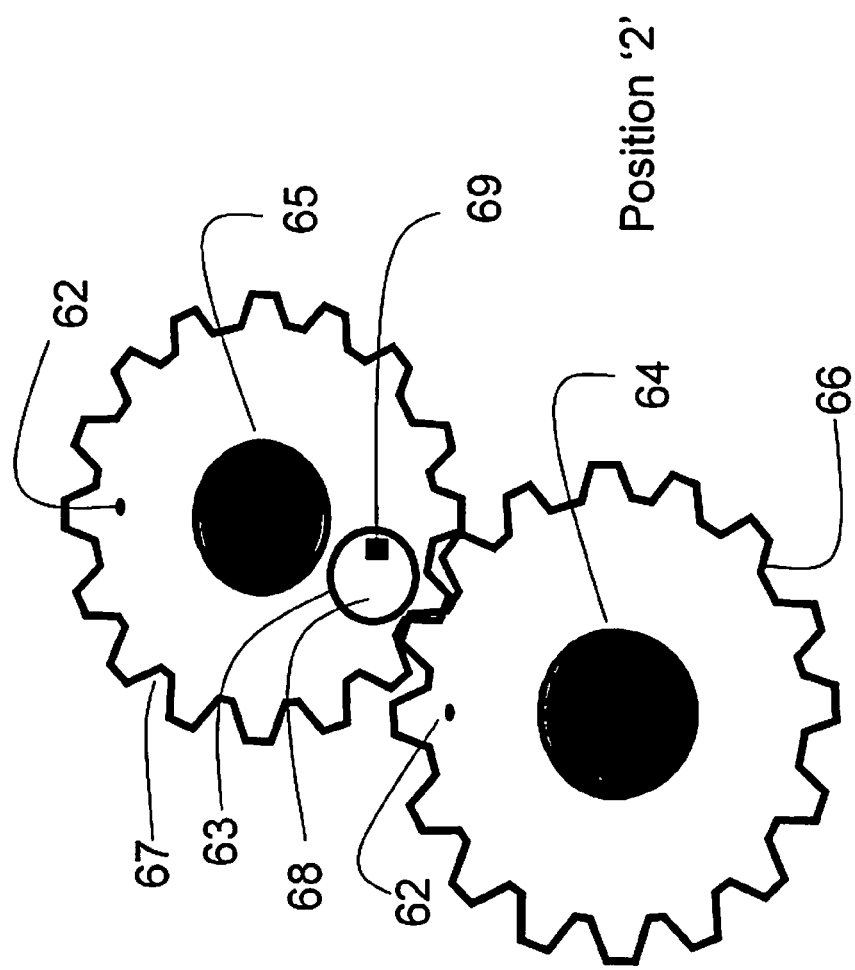

With reference to FIGS. 9A and 9B, there is shown a portion of mechanism for driving the structure of bowls 40, 42, 44. FIG. 9A shows a power shaft 64 connected to a rotating main gear 66 driving a second rotating gear 67 connected to unpowered shaft 65, FIG. 9A, Position 1. FIG. 9B is a view similar to FIG. 9A showing the gears rotated to a different position, Position 2, noted by the movement of index marks 62. The pin's 68 linkage to another structure (for example a bowl) prevents the pin 68 from rotating but does it allow it to gyrate about the axis of unpowered shaft 65, using a bearing 63, the radius of gyration is defined as the distance between the center of fixed shaft 65 and the center of pin 68. Thus, the dot 69 on the pin 68 stays oriented in the right side of the pin 68, gyrating, during the rotation of gear 67 as shown in FIG. 9B, Position 2.

FIG. 9C is a view showing nested gyrating structures, a bowl and two trapezoids, which are gyration driven by common power plant 64. In this figure the nested structures have an inversion of pathway length reflected in the two transitions 56; the bowl 40 transition 56 to trapezoid 42 is an increasing pathway, whereas the trapezoid 42 transitions 56 to trapezoid 44 is to a smaller pathway length. The gear analog is used to define how a common drive 64 can be used to control phasing (gear clocking) positions of gearing systems' to gear index 66X, and allow for different radii of gyration defined by center-to-center distance between 65B-68B, and corresponding for gears 65C-68C, and 65D-68D, and uses different gear ratios to defines different gyration frequencies. Phase variation is represented by different positions for the structures' gears '67B', '67C', and '67D' in relation to the main gears 66 with index marks 66X.

FIGS. 9A-9D show a geared system for imparting gyrational movement to the bowls 40, 42, 44. As shown in FIG. 9C a prime power plant's power shaft 64 drives three gearing systems (A-B, A-C, A-D), one for each gyrating subsystem, where 'A' refers to gears '66' and 'B', 'C', and 'D' refers to the gears annotated with those letters (for example 67B, 67C, and 67D).

The three identical 'A' gears 66 are connected to the prime power 64 shaft. Each of the three 'A' gears 66 has an index mark 66X. Each gyrating structure, bowl 40 and two trapezoids 42, 44, has its own gear to transfer power from the shaft 64.

Different gear sizes are shown for 67B, 67C and 67D ('B', 'C', and 'D' gears). The gear ratios defined by the sizes of 'B', 'c' and 'D' with respect to the size of gear 'A', reflects the gyration frequency; gyration frequencies are the gear ratios multiplied by the rotation frequency of the power shaft 64 driving gear 'A'. In FIG. 9C, the right-most gear D is smallest and will generate the highest rotation rate, and the highest gyration frequency. Index pins 68B, 68C, and 68D, counter-rotating, on each of the gears 67B, 67C and 67D will induce gyration of the attached structure (not shown due to drawing size of FIG. 9C). The attachment structure is shown in FIG. 9D.

Also shown are the relative clocking, with respect to the 'A' gears index marks 66X, of the individual smaller gears (B, C and D) in each pair with the offset of the lower bowl 40 from the trapezoids (they are not centered on each other) and by the offset of the trapezoids 42, 44 from each other. The discontinuity traps 56 are shown as centered on the lower frequency objects in this case. Exit 58 is where the media M departs the gyrating system.

Figure 9D:
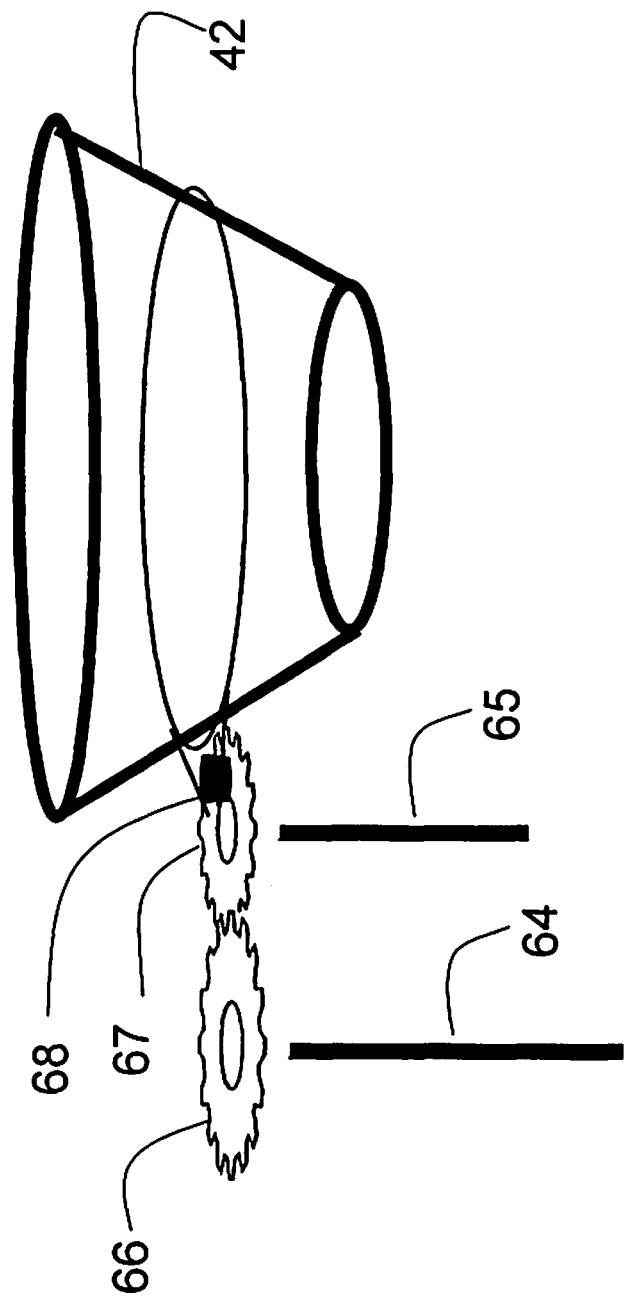

FIG. 9D shows the bowl 42 connected to the gyrating pin 68. Pin 68 gyrates about the fixed unpowered shaft 65, as gear 67 rotates with shaft 65. Gear 67 is driven by gear 66, connected to power shaft 64.

FIG. 9E is a schematic representation of off-axis force to impart gyration to a structure as broken down into its components. At the upper left quadrant 'A' of FIG. 9E, the prime power shaft 64 is rotating clockwise. The box-like structure 70 rotates with the prime power shaft 64. The cylinder-shaped object 71 counter-rotates (bearing or other low friction surface is used between box-like structure 70 and cylinder-shaped 71). The distance between the center-to-center of the prime power shaft 64 and the counter-rotating cylinder-shape 71 is the gyration radius. Box B is an exploded view of the rotating parts. C is a top view of the prime power shaft 64 (solid dark circle) with four rotation positions for the box-like shape 70 and the counter-rotating cylinder shape 71 (shown as an oval to denote gyration rather than rotation motion—it stays in the same orientation). The box D to the bottom-right is a representation of the gyrating structure, noted in box A as gyrating, in four different planar positions.

FIG. 9F shows an expanded view of a simple mechanism for inducing gyration motion without gears. Powered shaft 64 drives a plate 70 which includes the structure for counter-rotating (via low friction device such as a bearing) structure 71 connected to a gyrating structure. Gyration is induced because the counter-rotating structure 71 is mechanically over-constrained.

Figure 9G:
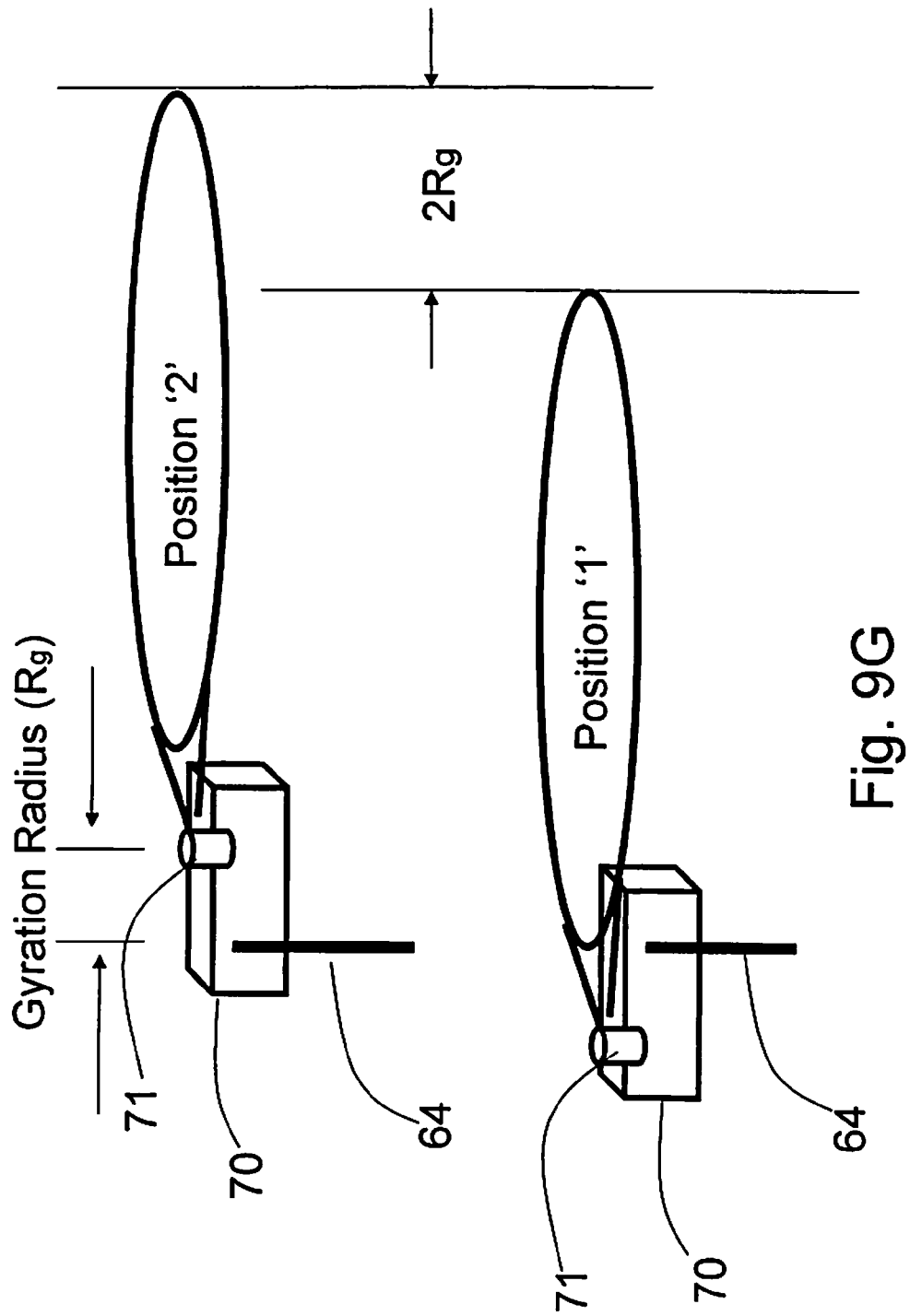

FIG. 9G has two positions of the mechanism from FIG. 9F. Shaft 64 is shown as rotated 180 degrees, as reflected in the right-hand edge of gyrating structure from position '1' as compare to position '2'.

Figure 10:
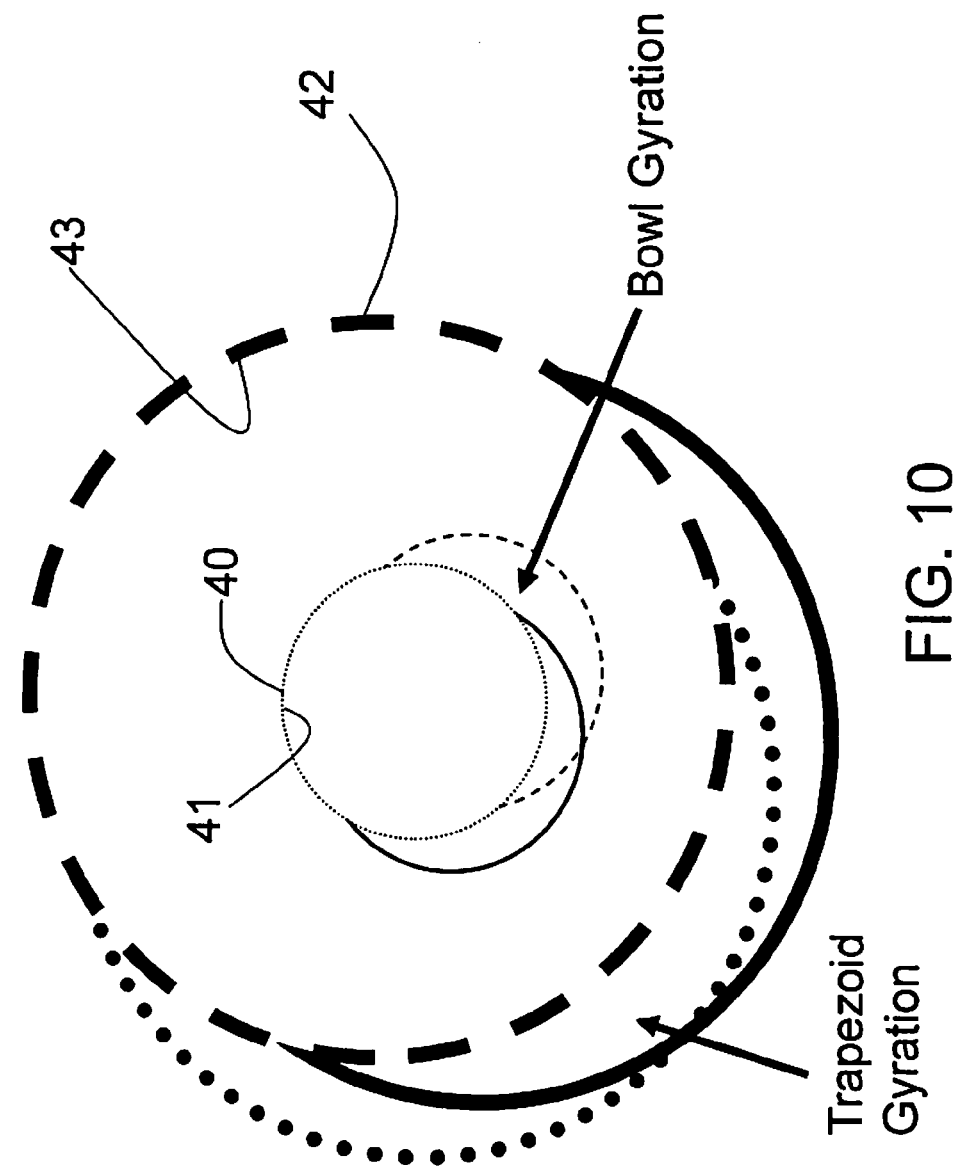

FIG. 10 shows three different positions for each of two surfaces, where the larger circles are three possible positions for a single surface, for example the inner surface 43 of the intermediate bowl 42 and the smaller circles represent the inner surface 41 of the lower bowl 40. Discontinuity traps are not shown but would be constructed to accommodate these dynamic envelopes.

Figure 11:
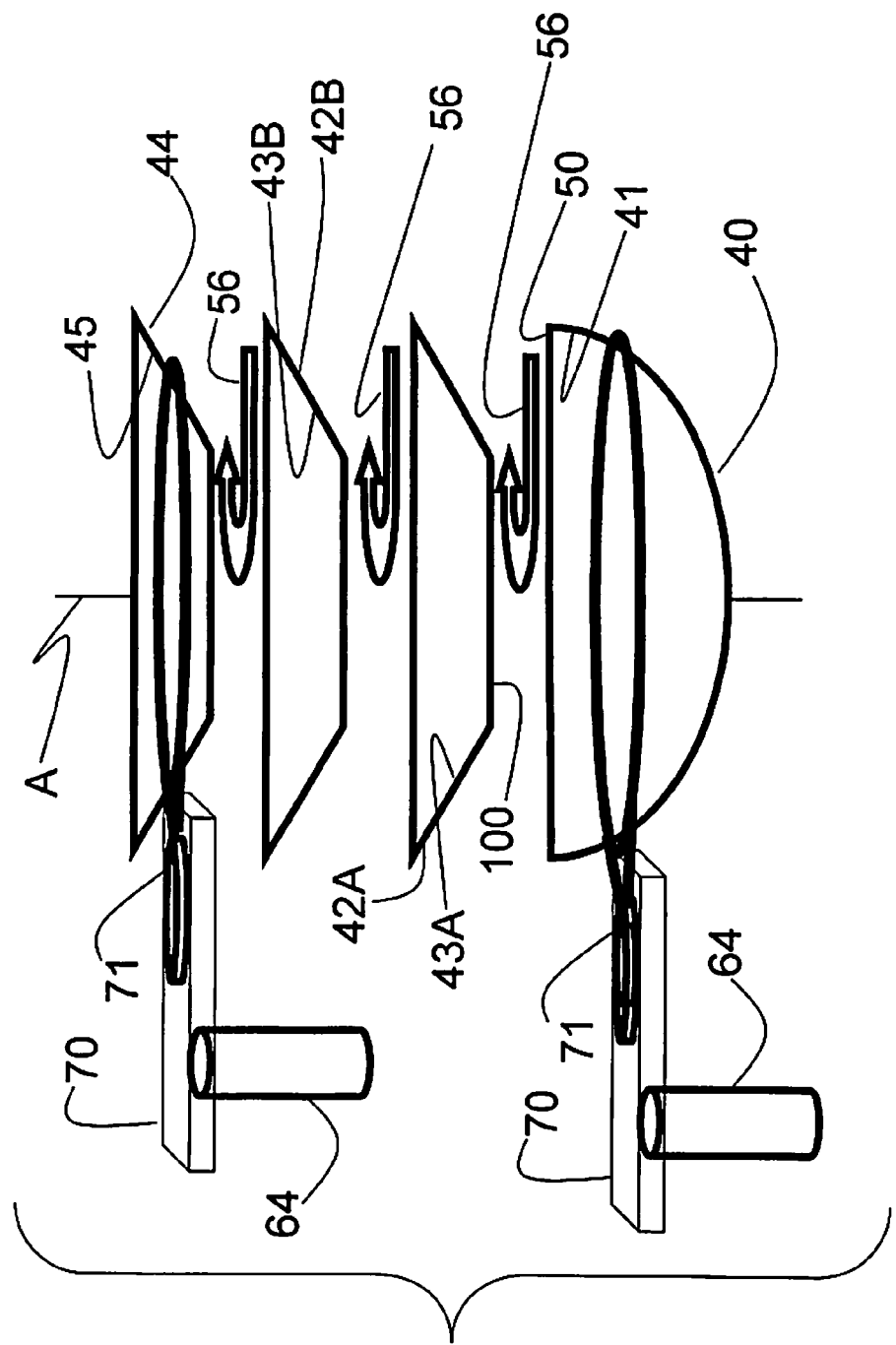

FIG. 11 shows a stack of lower bowl 40 and three trapezoidal shaped bowls (namely, two intermediate bowls 42A and 42B and one upper bowl 44 with inner surfaces 43A, 43B, and 45) in a stack aligned on a common axis A. Bowl 40 and Trapezoid 44 are shown with individual power plants' components 64, 70, and 71, as described in FIG. 9E-9G items 64, 70, and 71 Three (3) Delay Length devices (Discontinuity Gaps) 56 are shown between each of the stages; bowl-to-trapezoid and two trapezoid-to-trapezoids. Top of Bowl 50 is the start of the first discontinuity trap 56, ending at the bottom of trapezoid 42A 100 on interior surface 43A. This discontinuity gap is from a larger diameter bowl surface 41 to a smaller diameter trapezoid surface 43A.

Figure 12:
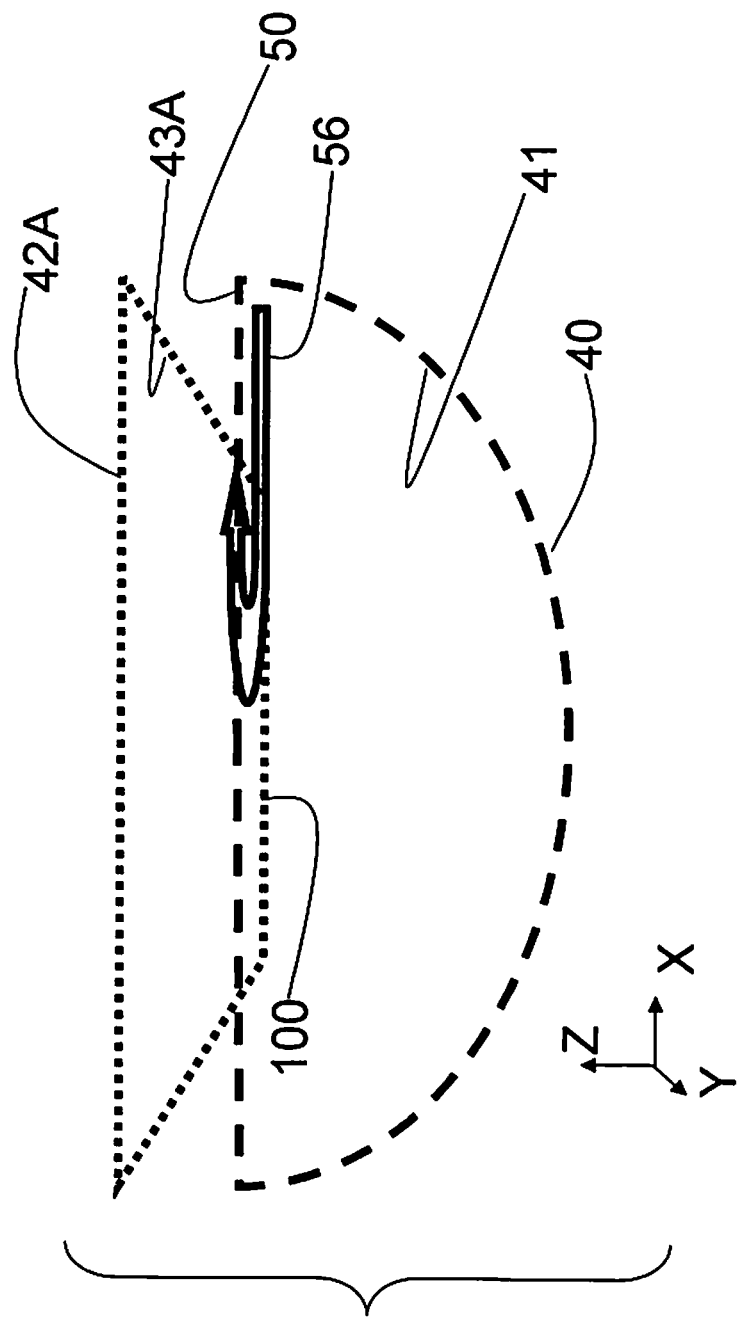

FIG. 12 is an expanded view of the portion of FIG. 11 where the bowl-to-trapezoid discontinuity trap 56 transitions media from the top 50 of the larger diameter bowl 40 with interior surface 41, at a lower gyration frequency, to a smaller diameter, higher gyration frequency, lower surface 100 of the trapezoid 42A with interior surface 43A. In this edge-on view the bowl, discontinuity trap, and trapezoid are overlapping, such that the bottom edge 100 of trapezoid is 'lower' than the top edge 50 of the bowl 40 in the 'Z' axis. The gyration plane is the XY plane.

Figure 13:
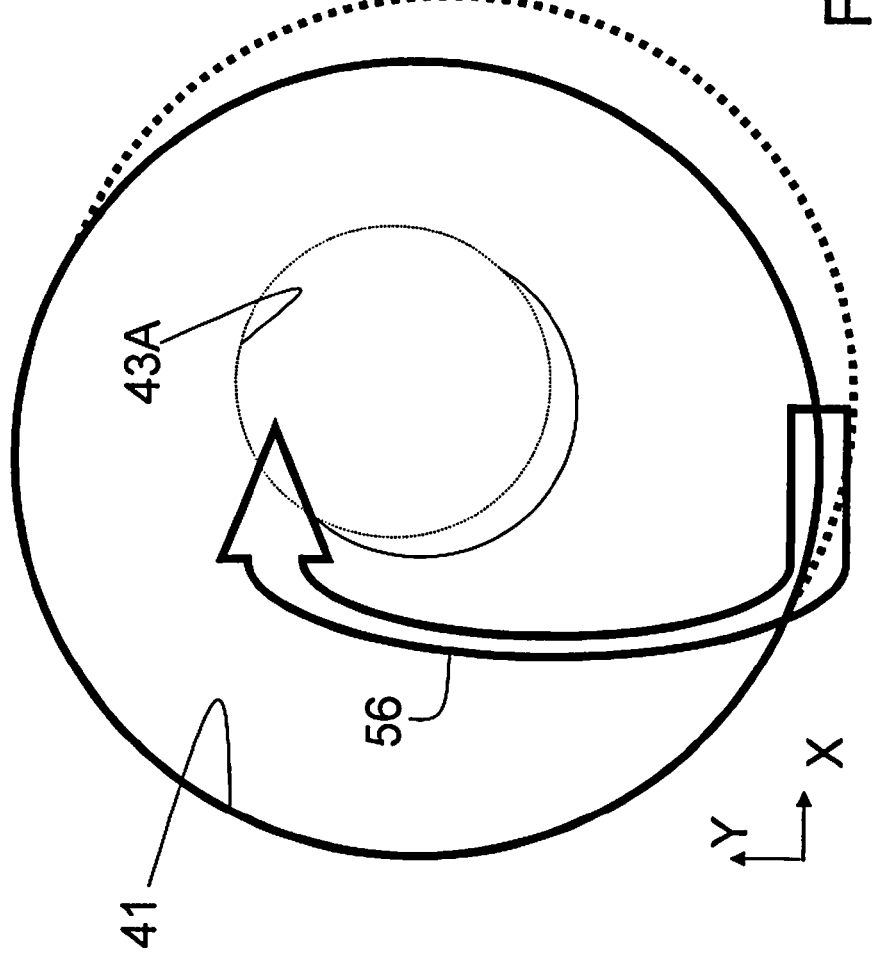

FIG. 13 is the 'Z' axis view of FIG. 12. The bowl has the larger diameter as surface 41, and the trapezoid is surface 43A. Two gyration positions are shown for the bowl and trapezoid.

FIGS. 12 and 13 show schematically the transition path followed by the media during gyrational movement of the stacked bowls with the media being carried from a larger diameter as it exits from the tops of the bowls to a smaller diameter as it is carried to the lower portion of the next bowl thereabove.

Figure 14:
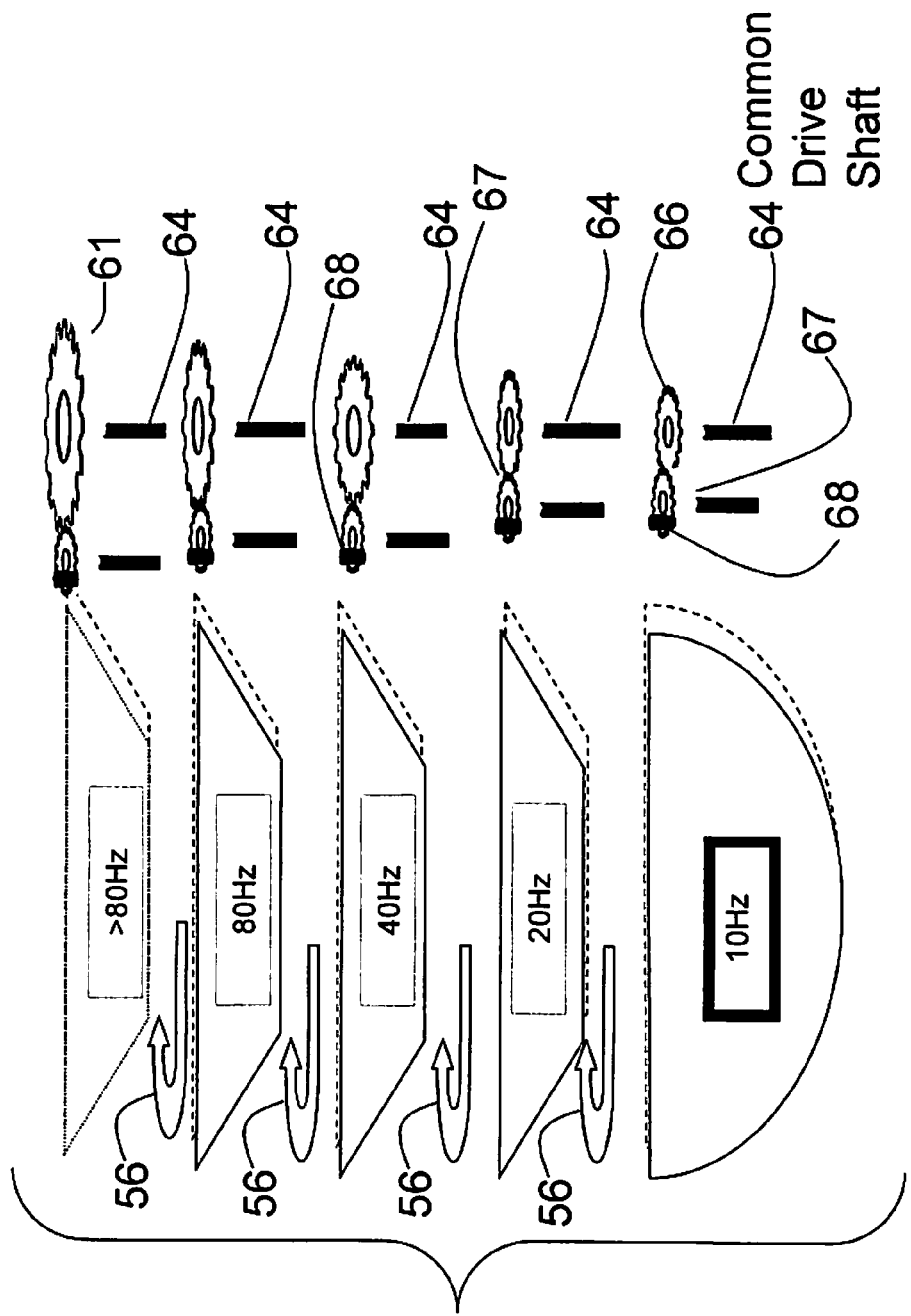

FIG. 14 shows a vertically aligned stack of a lower bowl and four trapezoidal shaped bowls aligned thereabove. Gear mechanisms for imparting gyrational movement are shown for each bowl. As can be seen, the driving gear for each bowl gets progressively larger from the lower to the upper. As shown, the lower main driving gear 66 is the smallest and gives the smallest gyration frequency (for example 10 Hz as shown) while the uppermost driving gear 61 is the largest and gives the highest gyration frequency (for example >80 Hz as shown). All the drive gears are powered from the same 'common drive shaft' 64. The gyration radius is the distance between the center of the second gear 67 and the center of the pin 68. Gyration motion is depicted as the dashed 'shadows' behind each structure, lower bowl and four trapezoidal shaped bowls. Bowl-to-bowl transitions, delay lengths or discontinuity gaps, 56, are shown on the left-hand edge of each bowl-to-bowl interface.

Figure 15:
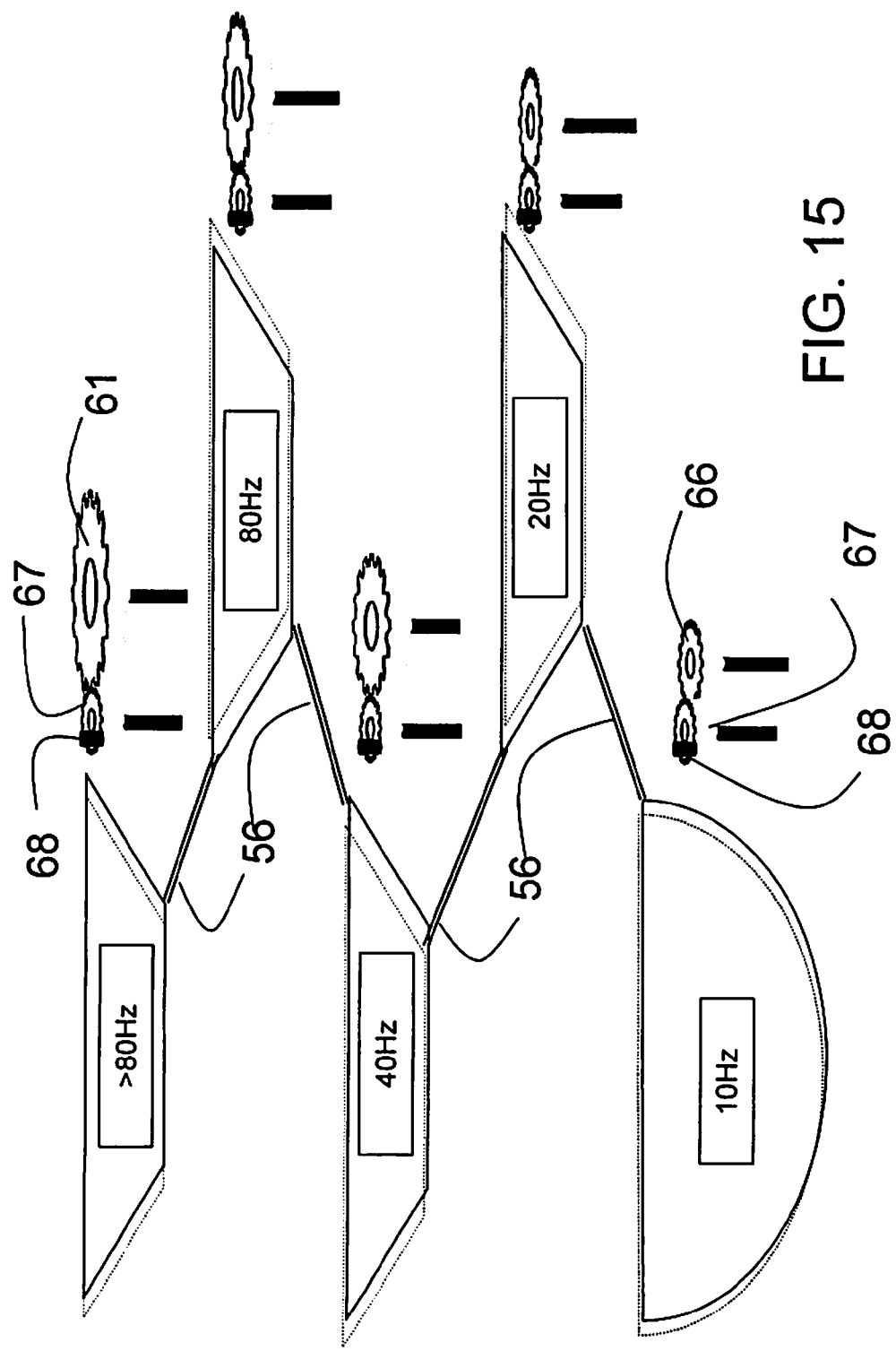

FIG. 15 is similar to FIG. 14 but showing the bowls offset from adjacent bowls. 56 are the transitions via discontinuity traps.

Figure 16A:
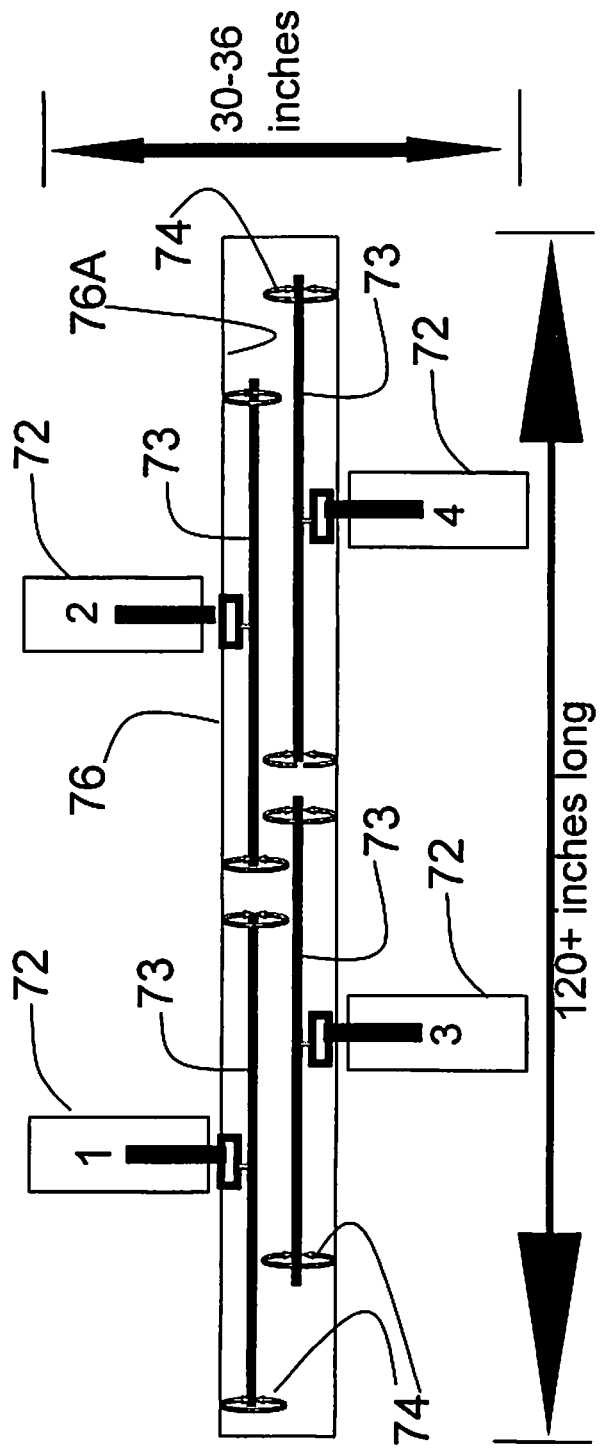
Figure 16B:
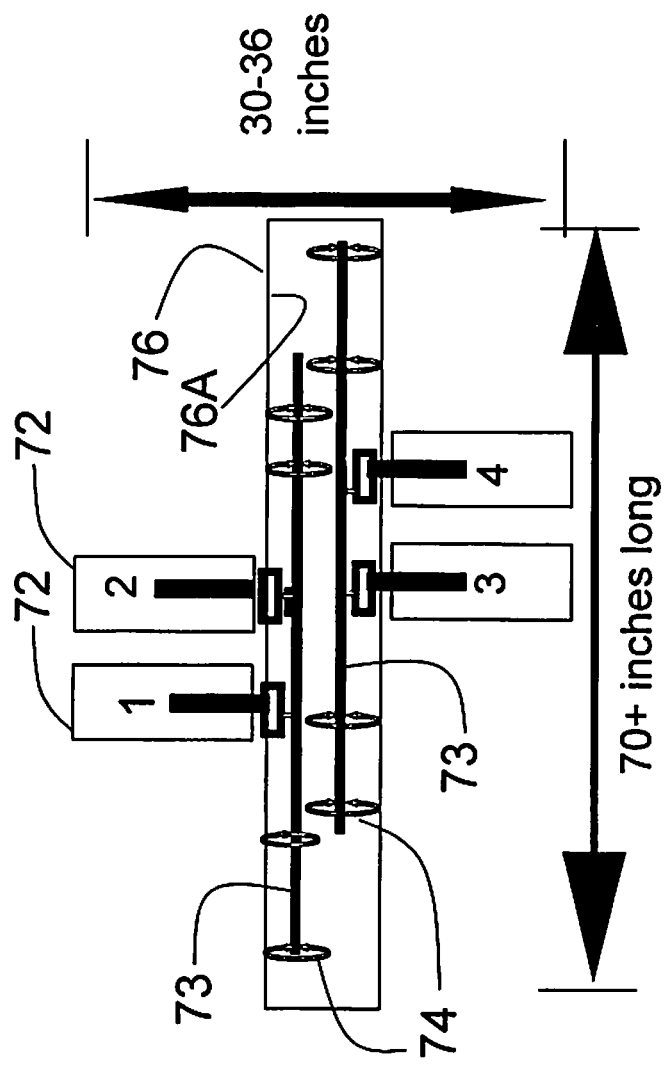
Figure 17A:
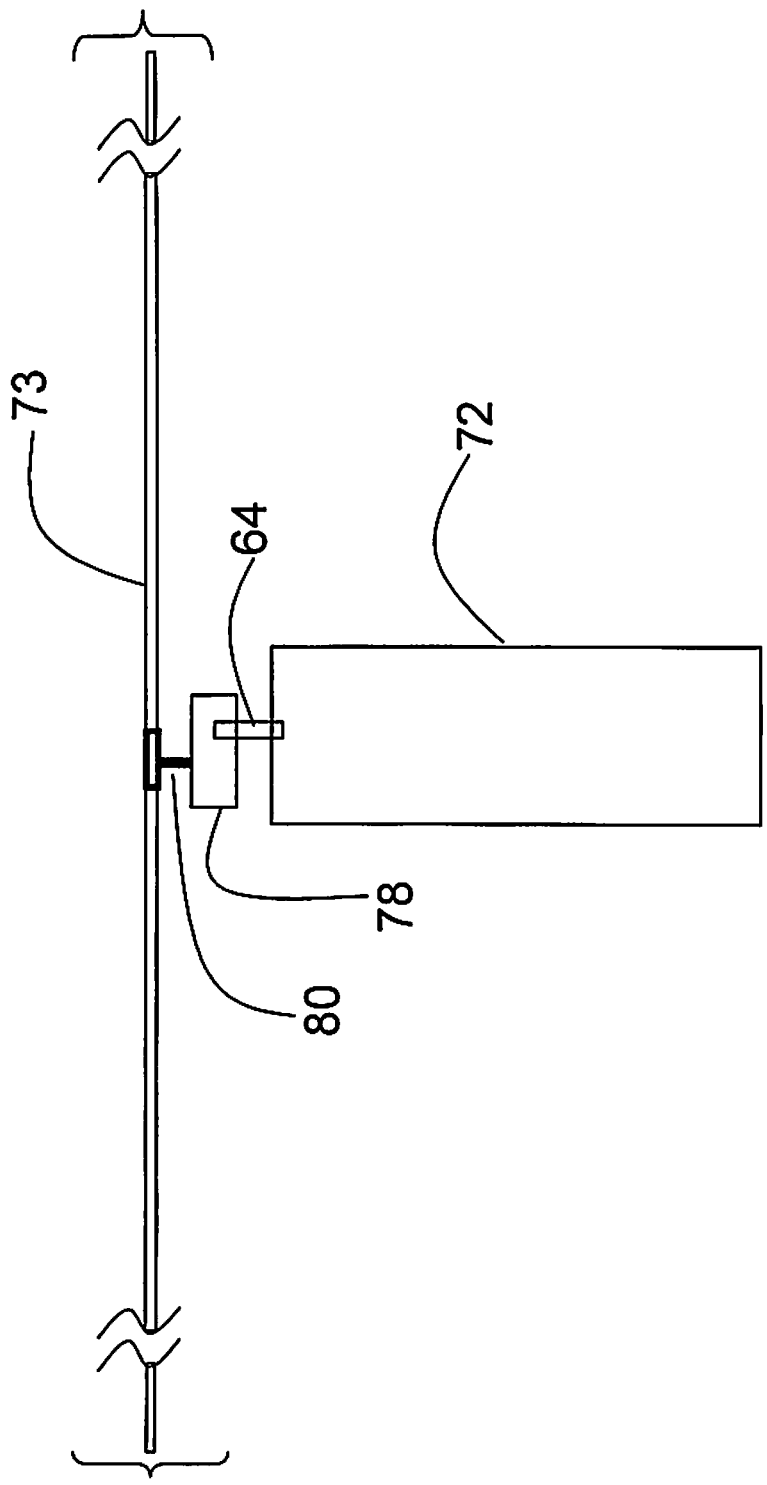
Figure 17B:
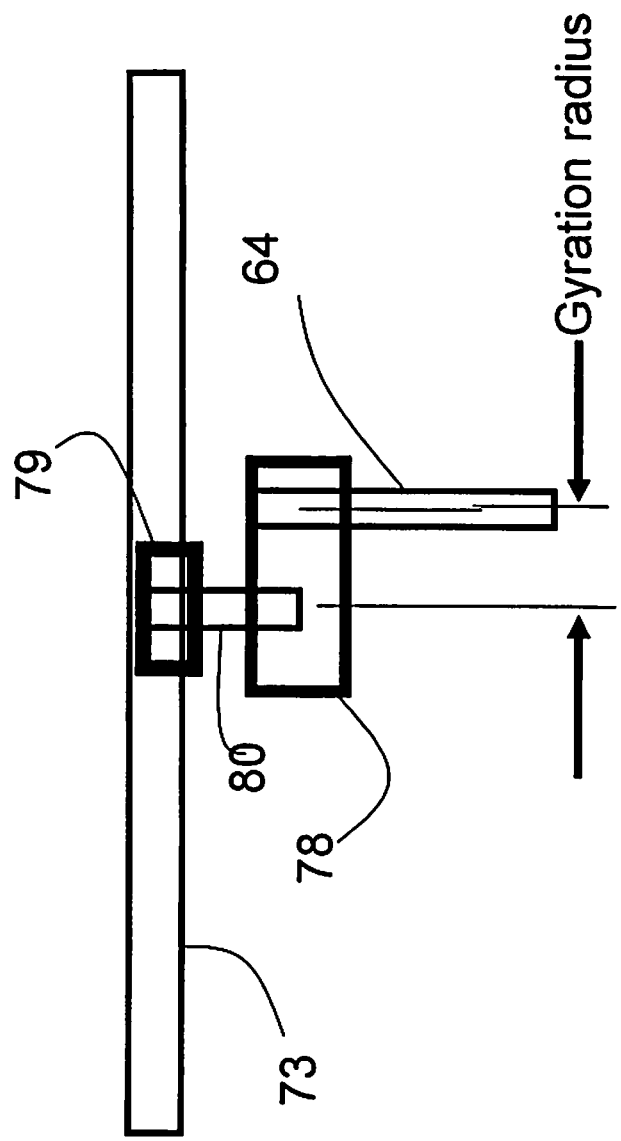

FIGS. 16A and 16B are front and side views of a four stage machine with four motors 72 for gyrating structures. Each motor 72 is connected to an individual rotation-to-gyration mechanism, gyrating a composite of two plates 73 with the arcuate pathways inscribed thereon and 'wobble control' bearings 74 located at the four corners of each composite structure 73 and attached to the inner surface 76A of protective enclosure 76. See FIGS. 19A and 19B and description related thereto. The thin structures 73 are in a protective enclosure 76.

FIGS. 17A, 17B, and 18A, 18B show details for the interfaces between the motor and the composite of thin gyrating plates 73. There is shown a motor 72 driving a power shaft 64. A connector 78/propeller blade is connected to the power shaft 64 and extends perpendicularly outwardly therefrom. A post 80 extends upwardly from the connector 78 along an axis parallel to and spaced from the axis of the power shaft 64. The connector 78 transfers rotating power to a bearing 79 mounted on the structure of the plates 73 to induce gyrating motion to the plates 73. The distance between the axis of the post 80 from the axis of the power shaft 64 is the gyration radius.

Figure 19A:
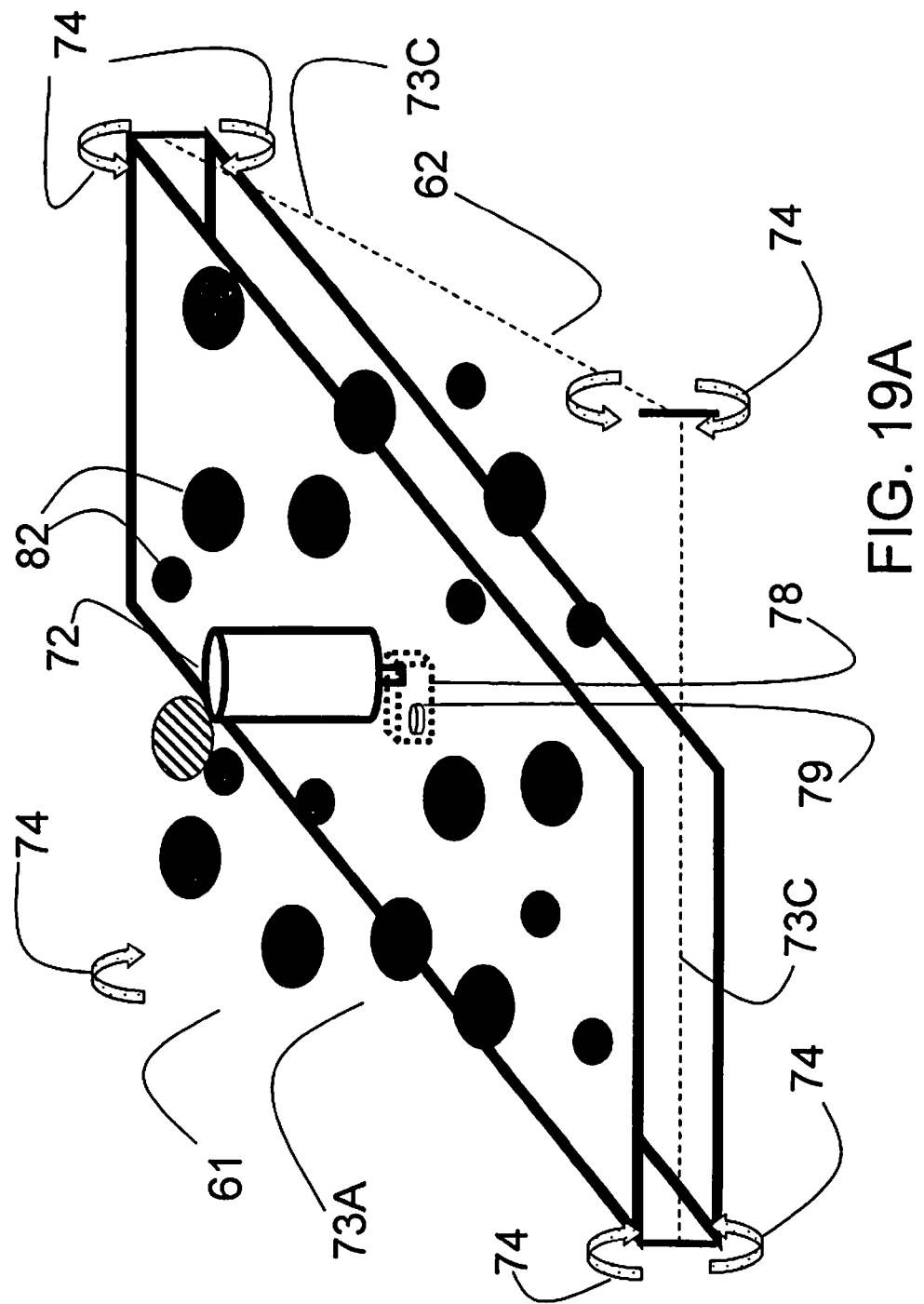
Figure 19B:
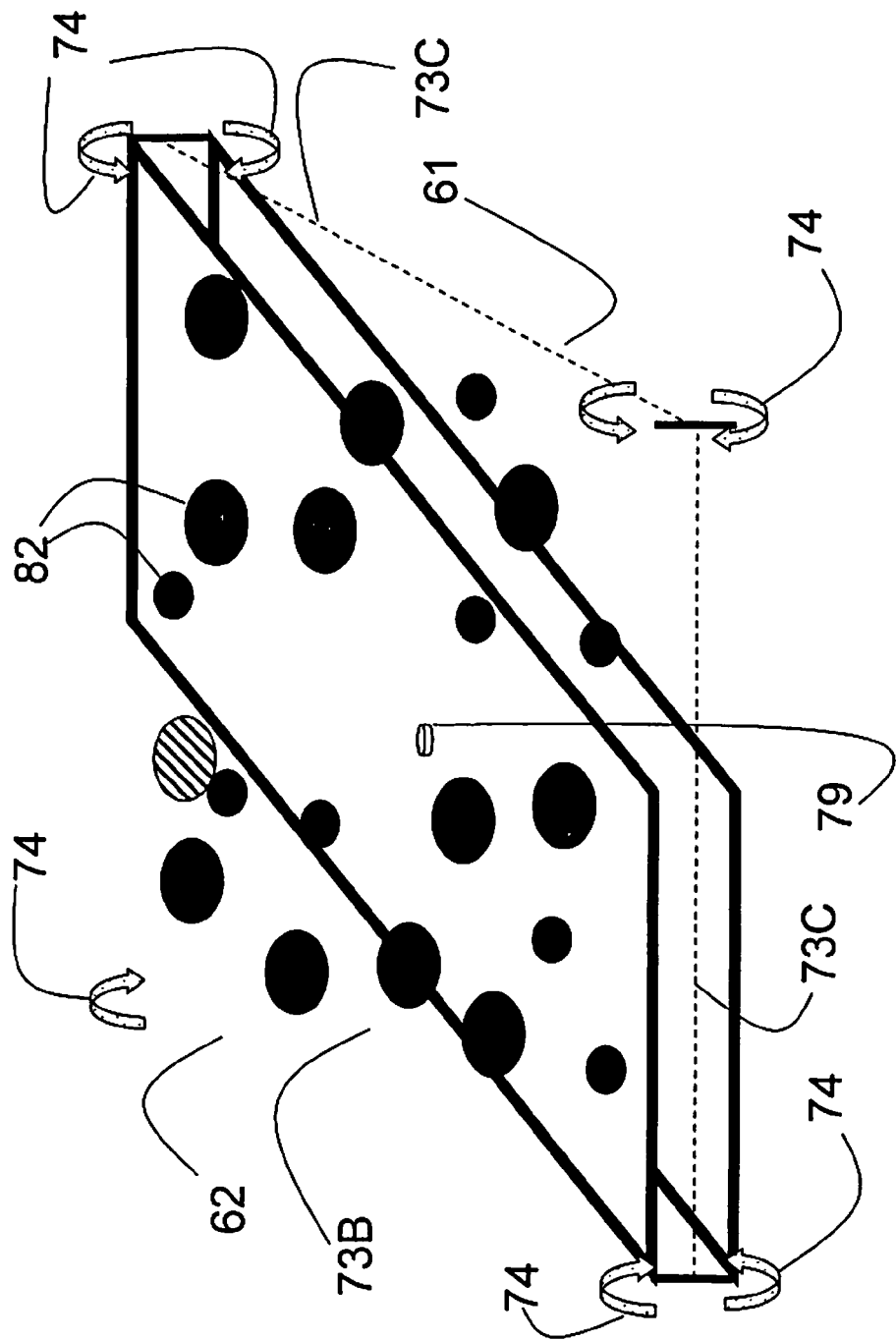

FIGS. 19A and 19B are drawings of one stage's large thin plates of a composite of two plates, namely, plate 61 (FIG. 19A) and plate 62 (FIG. 19B). The exterior surfaces 73A and 73B has mass removed therefrom leaving a series of spaced apart depressions 82. The others are effectively duplicates. Mass removal is critical to limiting the power demands of these systems. The placements of the depressions 82 are representative and do not have to be as shown in FIGS. 19A and 19B. Two plates 61 and 62 are mated, at the interface 73C, each having half of the arcuate pathway cut into it. These mated halves form a composite structure with a 'tunnel' for media to travel inside. The plates 61 and 62 form plate 73, as shown in FIGS. 16a, 16B, 17A, and 17B. At the mating interface 73C the interior surfaces of 61 and 62 are joined. Arcuate paths are inscribed to one or both of the interior surfaces of the plates 61 and 62 sufficient to contain there between media of the size desired to be propelled. Wobble control is a significant factor with one bearing 79 at the center of the large structure (moment arm length is about 1 meter), attached to motor 72 connected via 78/80 (80 omitted in this drawing but shown in previous FIGS. 17A, 17B, 18A, and 18B). At the corners there are bearings 74 of the wobble control device to carry the load and maintain planar motion as the media flows through the arcuate pathway (tunnel) between the plates. The media movement causes an ever changing moment of inertia. The transitions between stages are not shown.

Figure 20:
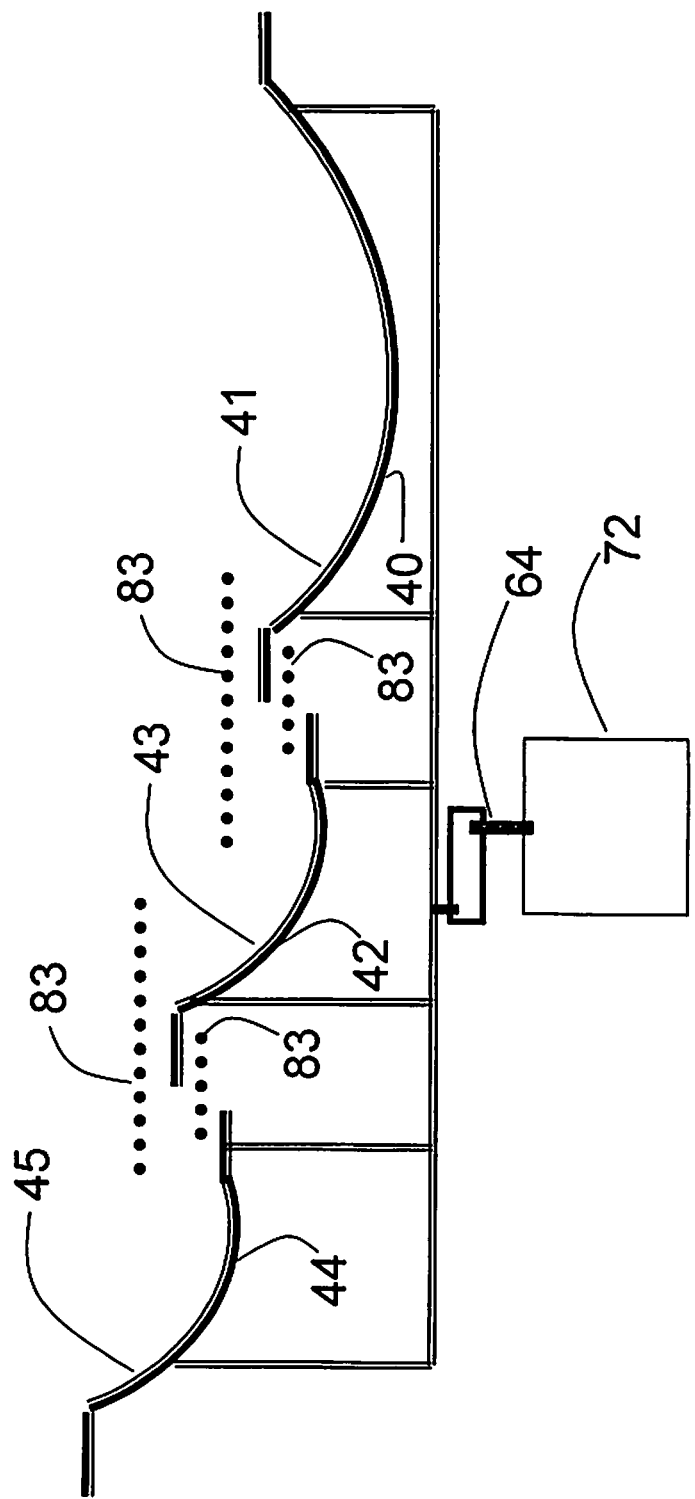

FIG. 20 is a cut-away view of a single gyrating structure with three arcuate surfaces; namely bowl 40 plus 2 annular rings 42, 44. Stationary structures 83 (shown by dotted lines) are delay lengths used to re-phase the media from one arcuate surface (i.e. inner surface 41) to the next arcuate surface (inner surface 43 and 45) in sequence. Gyration frequency and gyration radius are identical for all three arcuate surfaces 41, 43 and 45. The gyrating structures overlap stationary structures 83 sufficiently to always positively transport media to the next arcuate surface. Overlap is greater than twice the gyration radius. Motor 72 and power shaft 64 are shown, a more complete description is given in FIGS. 17A, 17B, 18A, and 18B.

Figure 21:
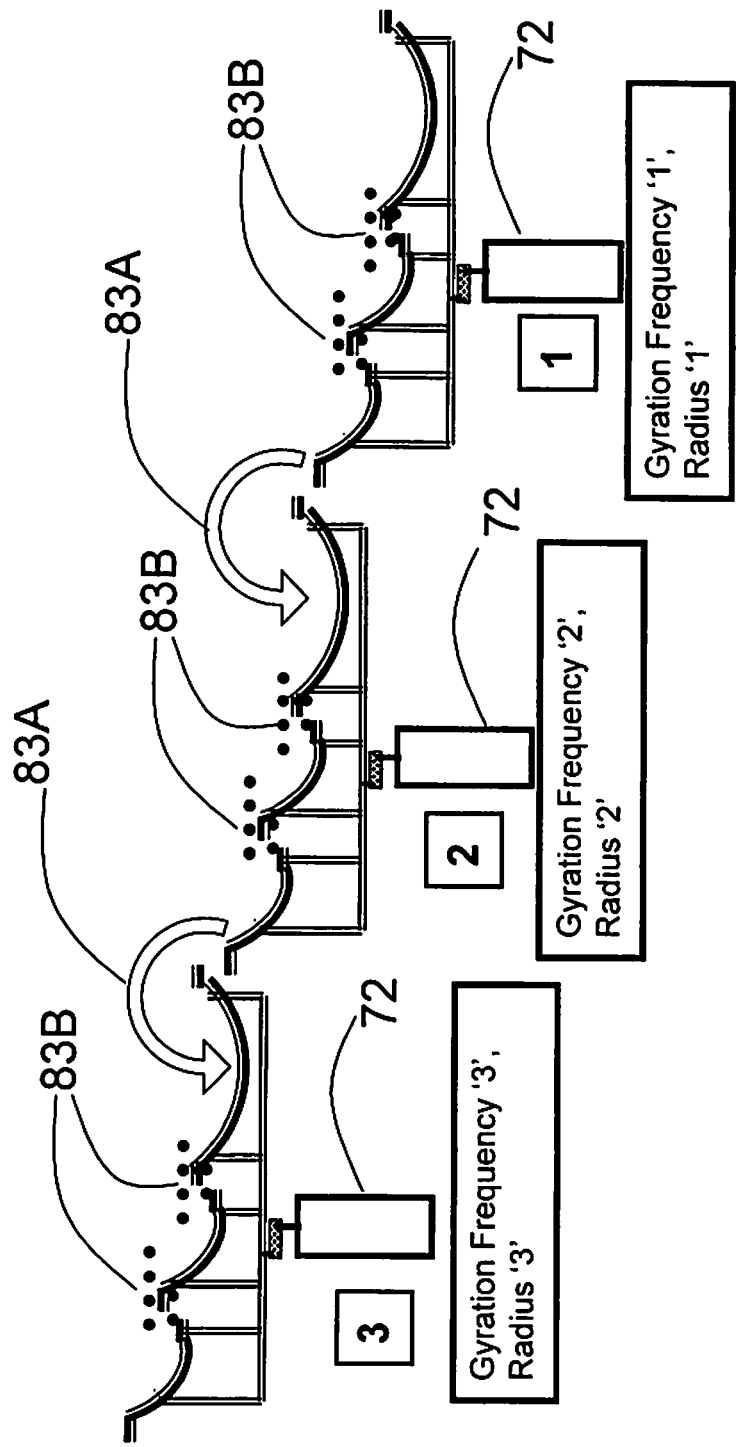

FIG. 21 shows three 'stages', each comprised of a motor 72 to power a gyrating subassembly connected to three arcuate surfaces (bowl 40 and two annular rings 42, 44 as shown in FIG. 20). Stage-to-stage media transport are stationary structures 83A and 83B. The stationary structures 83A and 83B perform two functions; namely, media transport between arcuate surfaces and phase offset as a consequence of media transit time in stationary structure. Besides rephasing, these allow gyration frequency and gyration radius to be different between stages. There are two types of stationary structures; namely, stationary structures 83A for delay lengths where different gyration and frequency and possible different gyration radius exist before and after the delay length and stationary structures 83B for delay lengths where the same gyration frequency and gyration radius exist before and after the delay length.

Figure 22:
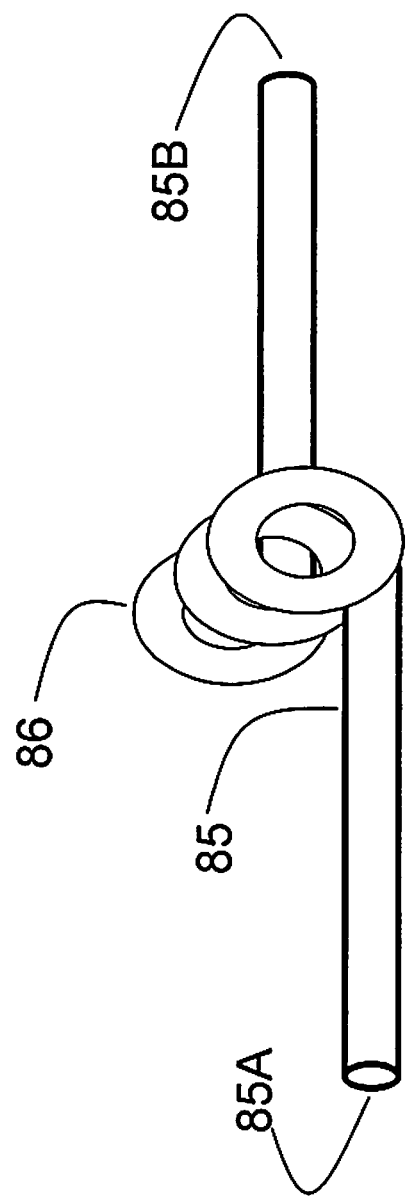

FIG. 22 shows 'zero' degree-of-freedom (DoF) delay path device. It includes a continuous conduit 85 extending from one gyrating structure to a second gyrating structure where the differences in gyration radii and gyration frequencies are mechanically absorbed in an out-of-plane 'service loop' device (where the plane is defined as the two axes of the gyration). Additional structures can be used to provide support of this device, but those additional structures are not part of the tube itself. One end 85A of the conduit 85 is hard attached to a structure having gyration frequency '1' and gyration radius '1'. The other end 85B of the conduit is hard attached to a structure having gyration frequency '2' and gyration radius '2'. A service loop 86 decouples the two gyration connections 85A, 85B associated with a transition device. The conduit 85 is continuous device induces a phase shift if within a gyrating structure (the delay loop for a child's hula hoop toy).

Figure 23:
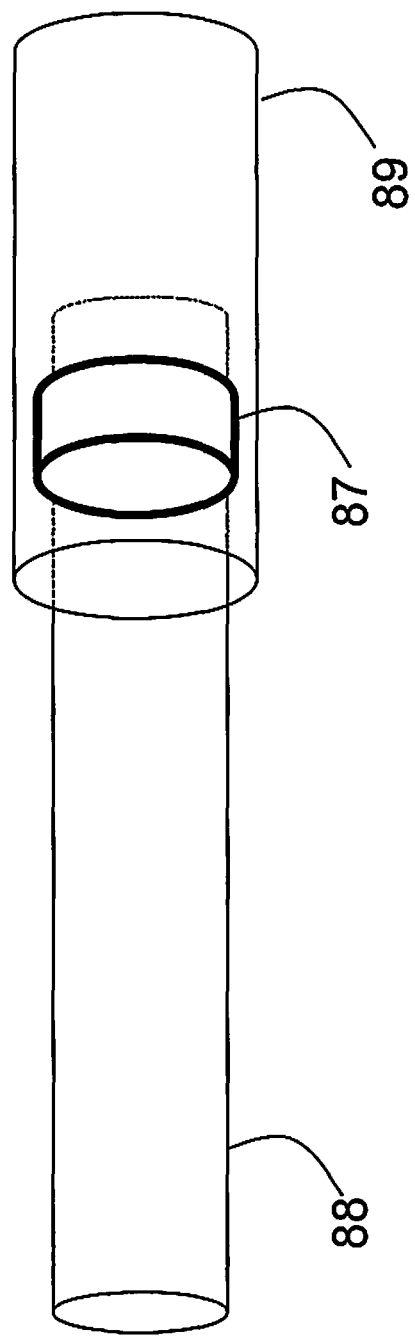

FIG. 23 shows a single, 'one' degree-of-freedom (DoF) delay path device. Gyration motion is decoupled into two one-axis motions; namely, one along the direction of media travel and the other perpendicular to media travel. The delay path device includes a smaller diameter tube 88 and a larger diameter tube 89 positioned between stages, for example from one bowl 40 to an intermediate bowl or section 42. The end of tube 88 away from tube 89 is attached to one stage (bowl 40 for example) and the end of tube 89 is attached to the adjacent stage (intermediate section 42 for example). Media is moving from left to right. One one-axis bearing 87 allows the smaller diameter tube 88 to 'slide' inside the larger diameter tube 89 accounting for motion in one dimension (along the axis of media motion). Structures gyrate at different frequencies and may have different gyration radii. Motion in the second dimension is accounted for by allowing the tubes 88, 89 to flex. Additional structures can be used to provide support of this device, but those additional structures are not part of the tube itself. Diameters of the tubes 88 and 89 are increasing from left to right to eliminate 'obstructions' along the media's pathway. The media jump an 'air gap' when they move from the smaller diameter tube 88 to the larger diameter tube 89.

Figure 24:
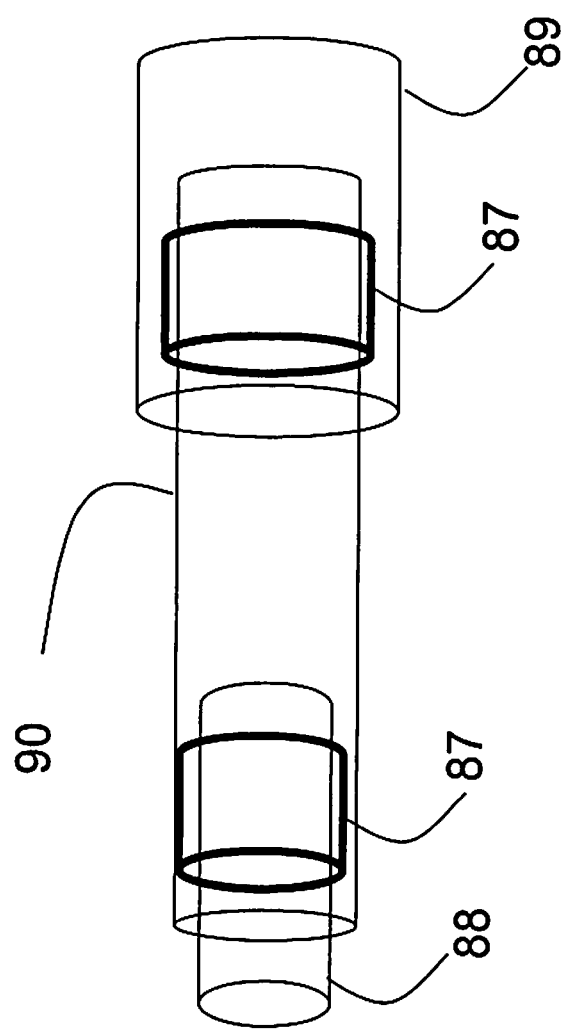

FIG. 24 shows two 'one' degree-of-freedom (DoF) delay path device. One end of the smaller tube 88 is hard attached to structure such as bowl 40. The opposing end of larger tube 89 is hard attached to an adjacent structure such as section 42. The delay path device is positioned between stages where the media is moving from left to right. Two one-axis bearings 87 allow the intermediate diameter tube 90 to 'slide' relative to tubes 88 and 89, thereby accounting for one dimension's motion (along the axis of media motion) while the smaller 88 and larger 89 diameter tubes gyrate at different frequencies, and possibly different radii. Motion in the second dimension is accounted for by allowing the tubes, predominately the intermediate diameter tube 90, to flex. Additional structures can be used to provide support of the intermediate diameter tube 90, but those additional structures are not part of the tube itself. Dampening devices along the intermediate diameter tube 90 isolate the two different gyrating structures from 'sensing' each other's motion. Diameters are increasing from left to right to eliminate 'obstructions' along the media's pathway.

Figure 25:
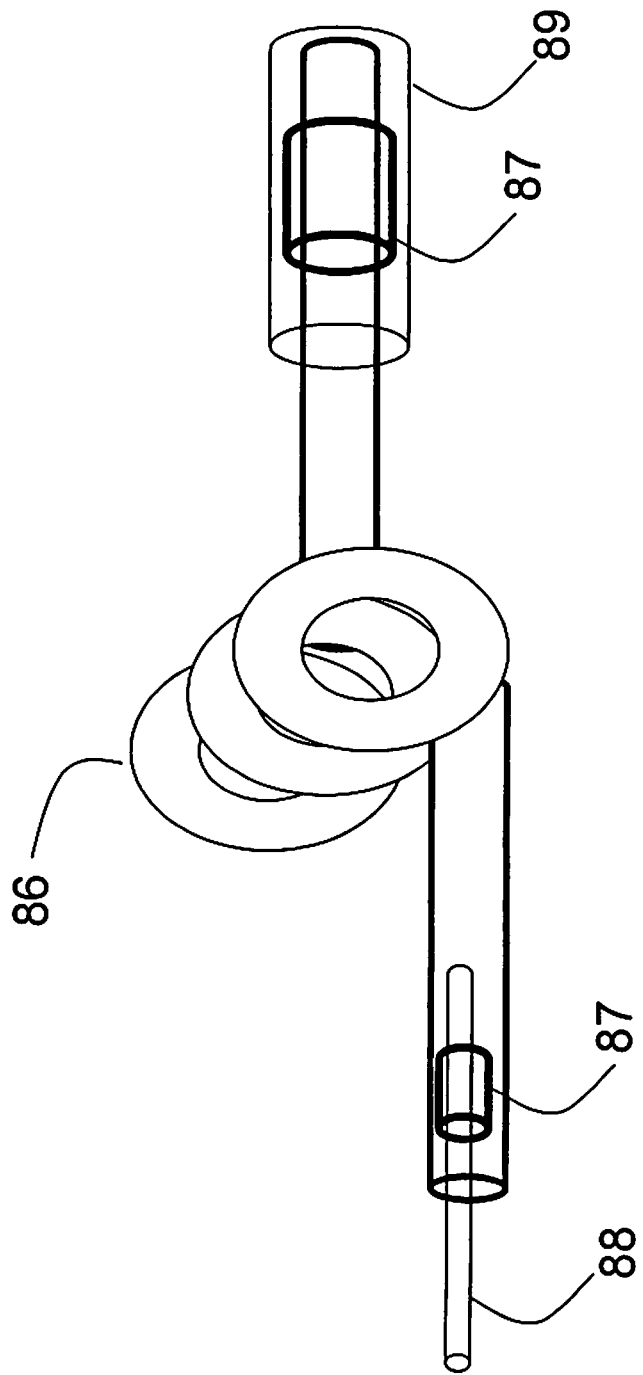

FIG. 25 shows two 'one' degree-of-freedom (DoF) delay path device as set forth in FIG. 24 but with the addition of a service loop 86. One end is hard attached to a first structure.

The other end is hard attached to a second structure. This combination includes a hard attached delay pathway at both ends with a 'gap' jump at each hard attachment and a 'service loop' 86.

FIGS. 26-29 represent delay length-only family such as a modified Hula Hoop. By adding one or more perpendicular delay lengths 12 to the classic Hula Hoop 10, as shown in FIGS. 26-29, new movements and visual effects can be added to this classic toy. To accommodate the potential of several delay lengths the original primary Hula Hoop pathway (roughly a 10 foot pathway of 1-2 inch diameter flexible plastic tubing) can be made as several 10 foot long smaller diameter tubing, either held together by an outer sheath or by twisting them like a braid. Each new smaller diameter 10 foot long tube/hoop 10 has one or more delay length(s) 12. The media moving inside the smaller diameter tubing becomes 'out-of-phase' with the human powering the hoop whenever it enters a delay length 12. This is sensed by the human as a 'wobbling effect'.

Figure 26:
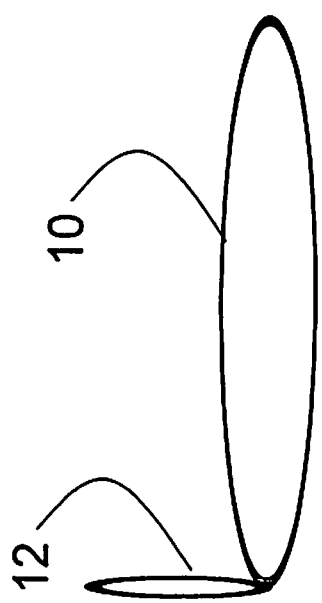

FIG. 26 shows a hula hoop 10 with exit into the perpendicular delay loop 12 and re-entry back into the hula hoop at the same tangential location (even as the entire hula hoop has gyrated some angle less than 360 degrees).

Figure 27:
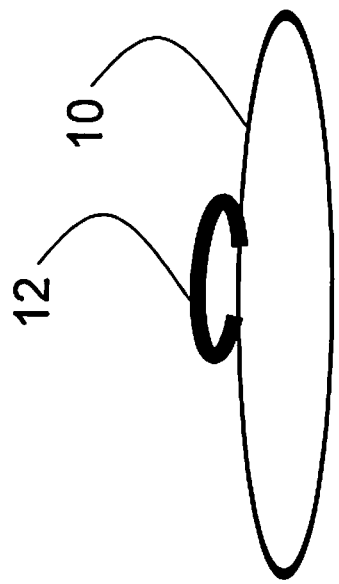

FIG. 27 shows a hula hoop with exit into the perpendicular delay loop 12 and re-entry into the hula hoop offset relative to the point of exit (even as the entire hula hoop has gyrated some angle less than 360 degrees).

FIG. 28 shows a hula hoop 10 with multiple perpendicular delay loops 12 and re-entries back into the hula hoop 10 at the same tangential locations (even as the entire hula hoop has gyrated some angle less than 360 degrees).

FIG. 29 shows a hula hoop 10 with multiple perpendicular delay loops 12 and re-entries into the hula hoop 10 with offsets relative to the point of exits (even as the entire hula hoop has gyrated some angle less than 360 degrees).

Many different devices, ranging in usage from toys to demotion tools, can be fabricated using specialized 'media' accelerated by gyrating machinery employing delay loops and delay lengths, and gaps. The media is what defines the real utility of the overall system performance. For example the Hula Hoop will probably focus on media that affects the visual aspects of playing with a hula hoop. If light emitting diodes (LEDs) are the media (similar to the LEDs in children's shoes) then various light patterns can be activated as the media is accelerated at relatively low velocity within the tubular pathways. At the other extreme are demotion tools where hard, sharp, and high velocity media are desired. Media can be found insitu, or can be specially fabricated for the application. In some cases the media changes upon 'activation' like a two-part epoxy accelerated in parallel channels and mixed during the post acceleration transit or upon impact with the surface of usage.

The following examples are just a few applications.

Hula hoop ideas include a series of channels within a conventional Hula hoop, nominally a meter or two in diameter, such that the media (assume LEDs or some fluid with color) will react to the variation in the velocity (change in position with respect to time), acceleration (change in velocity with respect to time), and jerk (change in acceleration with respect to time), caused by the media entering and exiting various delay loops. As the human makes the Hula Hoop lock at some fixed gyration frequency (generally no more than a few cycles per second) and at some gyration radius (possibly tens of centimeters), this defines the acceleration profile, various patterns will emerge from the superposition and/or transposition of colors and lights inside the hula loop 10 and the delay lengths 12 attached to the hula loop. Unlike a traditional Hula Hoop this design is capable of having an entrance and/or exit portal for media that is allowed to recycle from an external supply. It is also practical for these colored fluids and/or LEDs to be permanently trapped inside a closed loop system with delay length(s).

A medical device can be built with both of the features, delay lengths and "discontinuity" gaps. The media is typically going to be microscopic in size since it is entering the body; macroscopic (visible to the unaided eye) objects like needles and scalpels cause damage when entering a body. Many options exist for media to 'bore holes' or 'cut' different tissue types within a human body. A very small candidate media is a Ferritin (multi-folded proteins used in many biological functions at the individual cell level) either left as harvested or modified. At 15 nanometers in diameter the individual ferritin will have almost no momentum even when 'filled' with water or hydrogen peroxide; so the effectiveness of hole boring and/or cutting will depend upon the repetition rate of multiple ferritins impacting the tissue. High frequency gyration and multiple parallel channels will be employed to increase the repetition rate. A typical target site could be a cancer cell cluster (individual cell is 10-100 microns or micrometers, approximately 1,000 times larger than the diameter of the ferritin).

A four to six structure machine using the features described in FIGS. 11, 14, 15, 20 and 21 could accelerate small media (such as a ferritin) to many hundreds of meters per second. The lowermost structure gyrating at the lowest frequency (in the 5-15 hertz range) could be a 15-20 centimeters diameter bowl and two annular rings like FIG. 20. Three to five subsequent structures designed with annular rings or cones, with the highest having a frequency range between 100-1000 hertz, like FIG. 21 will delivery sufficient media to bore a very small diameter hole to the target mass. This highly compact arrangement is small enough to fit inside a medical operating suite and also allows pre-use cleaning to be completed within a modest sized facility (medical waste is critical to managing the process of getting certification). Greater exit velocity can be achieved by increasing the diameter or by increasing the gyration frequency. The power to move the structures can be internal or external, and geared or shaft driven, as shown in FIGS. 15 and 21.

The media is supplied to the lowest frequency first structure by a conventional intravenous (IV) bag or some other medically acceptable delivery system.

The medical applicator, at the exit of the gyrating machine, will direct projectiles, at velocities possibly approaching Mach 1, toward very specific body locations. Multiple IV bags can be used, with different size media, different types of media, and even mixed media supplied simultaneously on different channels. Selection of the sequence of media use will be unique to each case; larger mass objects might be used to generate the hole in one patient but not in another. Even at 300 meters per second a ferritin is only able to penetrate the patients' tissue to a very limited depth, thus larger media might be used to 'open' the pathway through the tissue to get to the target site for treatment. With high repetition rates, hundreds to thousands per second (or more), hole-boring media can reach places no other surgical tool can reach while minimizing collateral damage to adjacent tissue. These hole-boring media can be filled with water or other small molecules. Once the tunnel to the desired body location (such as the non-operable tumor's surface) is completed this pathway is used by subsequent treatment media to kill the tumor (localized cell poisoning).

Larger objects, still very microscopic, can be used. Drops of various fluids are obvious candidate media. Metals are another media of high utility, they are toxins and are manufactured at sizes ranging from 10 nanometers to macroscopic sizes. Some specialized metal processing preserves the metal as a core insulated by an oxide layer.

A highly credible toxin is nano-silver. Nano-metals have been in production for 20+ years, commercially available in sizes as small as 10 nanometers. Nano-silver is currently being used in bandages for medicinal purposes; nano-silver kills bacteria as the bacteria absorb the silver across their cell membranes. Other nano-metals can be used instead of nano-silver, as well as radioactive nano-metals. Generally these nano-objects are ellipsoids, thus they should 'flow like a sphere', especially if added to a fluid like saline or water. A secondary benefit of these nano-metals is the combustion (oxidation) which will act to locally heat up the tissue.

Hole boring can be used to address non-life threatening medical conditions that require the breaking of or depositing something onto the specific location within the body. This includes treatments to critical organs, hard-to-reach body parts, such as along the spinal cord, or where surgery has high chance of damage or debilitation. Additionally, hole boring can be used to treat bone spurs, make inoculations, break-up kidney stones, deliver drugs and many other medical treatments.

Hole boring can be used to imbed or affix microscopic or macroscopic objects, such as tracking devices into animals or into everyday objects (automobile bumpers).

Boring tools as described in our U.S. Pat. No. 7,013,988 will be able to use media of many different descriptions. The basic concept set forth in those applications was a boring tool that was powered remotely by a momentum 'projectile'. This momentum projectile can also be described as the media M in this patent application. As stated previously the size of the device will be a major factor in the utilization of the machine.

Abrasion devices are another market that can benefit from this patent. When not boring a hole a media M can be performing simple abrasion. Abrasion tools of many different sizes and design features are possible applications. A product using FIGS. 16-19 will remove/braze the hardened residual concrete located inside mixer truck drums and fixed site drums. Momentum of a bullet is exemplar of what can be done using a machine of the design and dimensions of FIGS. 16-19. These are transportable over roads and are deliberately designed to survive mishandling. The media might be metal ball bearings or stone, or even fluids. The media selection will be part of a market analysis, some will be reused others will be one-time use media. The design of FIGS. 16A and 16B use electric motors, readily available and highly reliable, making this design self-contained with one electrical hook-up as its only external interface beside the surface being targeted. This configuration can be transported over roads and is deliberately designed to survive mishandling.

Power-take-off (PTO) devices, common on construction equipment such as backhoes and forklifts, are a likely power source. Designs following FIG. 21 are more compact and therefore probably more compatible with PTO applications. Media selection is also market driven Portable smaller abrasion tools for consumer use (home applications) are also planned. The smaller tools are going to be power limited and as such the trade-off will be more about packaging and power than about exit velocity of the media. As rechargeable battery technology improves the range of home tools will expand. A water jet lawn mover, where the very small water jets have limited range due to momentum limitations, is an example. Floor and tile cleaner devices are also planned.

A more obtuse application is the Artic Ocean ice cracker design. This machine is also space-limited (volume-constrained), since the machine may only be deployed in small-sized submarines which receive their power via a cable attached to a cargo ship. FIG. 14 is the best choice for a volume-constrained application, but using the in-line approach versus the vertical stack shown in FIG. 14. The media for the ice cracker design can be ocean water. For the ice breaker application jets of high velocity water are fired from beneath the ice upwards into the ice and thereby cracking the ice (hence, the name ice cracker). The ice is mechanically supported by the water beneath it and cracking the ice from above is more challenging due to the incompressibility of the ocean beneath the ice. The machine will fire jets of high velocity water from beneath the ice to crack the ice, the highly compressible atmosphere provides almost no support to the ice from forces coming from underneath. Weakening the ice by cracking with high velocity water jets will allow for more ships to perform ice-breaker functions.

Burying underground cable and providing holes for thermal exchange devices coupled to the earth as a heat sink are other applications. For both applications it is advantageous to use the remotely powered boring bits from our previous patents, U.S. Pat. Nos. 7,013,988 and 7,500,477.

Currently it is not financially and physically feasible to create a conduit to a heat-sink due to the inability to go deep enough with multiple small diameter holes. Multiple small holes with deep depths create better coupling to the earth's heat sink; heat transport is surface area dependent and a single large diameter hole has less surface area then many smaller holes of equal cross sectional area. Additionally, the larger the hole-to-hole separation the greater the isolation of each heat sink, improving overall performance of the heat exchange.

For burying cables the ability to go long distances horizontally, in a straight line, with small diameter holes, and at deep depths is currently very hard to do. With a boring bit remotely powered by momentum projectiles, it is easy to attain the above desired attributes for burying cables.

The basic idea of a discontinuity is to allow the values for the key parameters (gyration frequency, gyration radius, phase angle, and absolute path length) to be adjusted in a single machine. Consider FIG. 6, imagine the lowermost bowl has a diameter of one meter and a height of 0.5 meters (height is almost immaterial for the concept development). A ball bearing placed inside the gyrating bowl will gain velocity provided the conditions are right and eventually exit the rim if not constrained in some way. The constraint is a channel or tube-like structure that will force the ball bearing inward to the first discontinuity; this is an example of going from a larger radius to a smaller radius. At the bowl's rim the ball is moving at a velocity of Pi×Diameter×Gyration frequency=3.14×1 meter×5 Hz which yields a value of about 15 meters per second. The first jump will occur, and the ball will be inside the small end of the megaphone, which is gyrating at 10 hertz. The first trapezoid's lowermost diameter is sized to be a stable velocity of 15 meters per second; this happens to be half the diameter of the bowl. Because the ball is being subjected to a higher gyration frequency it will gain velocity and climb up the inside wall of the trapezoid. At the uppermost portion of the first trapezoid the ball will be travelling at 30 meters per second. Repeating this process will continue to add velocity to the ball bearing.

This design has several key advantages: matched velocities on each side of a discontinuity and common parts in the design (manufacturing consideration). The prime power can be central, actually along the center line of the device, with gearing to producing the change in gyration frequency. It also has the option for phase shifting which comes for "free" with a discontinuity based design.

Phase shifting has a secondary benefit, it allows the ball bearing to be kept slightly out of synch with the nominal acceleration profile and therefore to be accelerated to velocities higher than projected by the simple 'matching calculation' defined above.

In all of these examples the system can have parallel pathways, each accelerating a mass and the mass can be different values, densities, size etc. . . . The exit portals can be at different locations such that different masses are allowed to exit at different locations.

Various types of projectiles can be used, noting that frictional forces will have to be addressed to keep the overall design practical. Flow materials, fluids of almost any nature (water to oils etc.), also become projectile mass. These flow materials are capable of carrying other objects such as solids that don't slide or roll easily. Solids that sublimate are a special class of mass to move inside one of these various gyrating mass accelerators.

The above detailed description of the present invention is given for explanatory purposes. It will be apparent to those skilled in the art that numerous changes and modifications can be made without departing from the scope of the invention.

The invention claimed is:

1. A mass accelerator for discharging projectiles comprising:
   (a) a plurality of structures each having an arcuate surface for supporting projectiles movable relative thereto, said structures being positioned one above the other from a lowermost structure to an uppermost structure, with one or more intermediate structures therebetween, each said structure lying on an axis and being movable such that said arcuate surface moves along a local radius of curvature when said projectile is located thereon to impart acceleration to the projectile;
   (b) a means for directing each projectile to the next adjacent arcuate surface upon reaching an exit portal at the upper area of said arcuate surface for that structure, said directing means forming either (i) a delay path or (ii) a gap to be spanned in the movement of said projectiles from one arcuate surface to an adjacent arcuate surface; and
   (c) at least one discharge outlet on the uppermost of said arcuate surface structures.

2. A mass accelerator according to claim 1 wherein the structures defining each said arcuate surface lie on a common axis.

3. A mass accelerator according to claim 2 further including a sensing system for causing said projectiles to be diverted from one pathway to another pathway.

4. A mass accelerator according to claim 1 wherein the structures defining said arcuate surfaces lie on different axes.

5. A mass accelerator according to claim 4 wherein at least two of said different axes are spaced apart and parallel.

6. A mass accelerator according to claim 3 wherein the arcuate surface of at least one of said structures includes means defining a plurality of pathways.

7. A mass accelerator according to claim 6 wherein each of said plurality of pathways has a discharge outlet.

8. A mass accelerator according to claim 7 wherein the discharge outlet for one of said pathways is offset from the discharge outlet of at least one other pathway.

9. A mass accelerator according to claim 8 wherein at least one of said pathways is sized to direct the movement of larger projectiles than other of said pathways.

10. A mass accelerator according to claim 1 wherein each said arcuate surface lies on a circle with the radius of the circle for at least one of the arcuate surfaces having a radius different than the radius for an adjacent arcuate surface.

11. A mass accelerator according to claim 3 further including a sensing system for causing said projectiles to be diverted from one pathway to another pathway.

12. A mass accelerator according to claim 1 wherein at least one said arcuate surface has radii of increasing length from the lower most portion of its structure toward the adjacent upward structure.

13. A mass accelerator according to claim 12 wherein one or more of said arcuate surfaces lies on a section of a cylinder.

14. A mass accelerator according to claim 12 wherein two or more arcuate surfaces lie on a section of a cylinder, cone or bowl of the same size.

15. A mass accelerator according to claim 1 wherein at least some of said arcuate surface follows a non-circular path.

16. A mass accelerator according to claim 1 wherein at least some of said arcuate surfaces are less than 360°.

17. A mass accelerator according to claim 1 further including power mechanism for imparting gyrational movement to each said structure.

18. A mass accelerator according to claim 17 wherein the frequency of gyration at least one of said structures is different from the frequency of gyration of other of said structures.

19. A mass accelerator according to claim 17 wherein the frequency of gyration of said structures is greater for higher structures than structures therebelow.

20. A mass accelerator according to claim 17 wherein the radius of gyration of at least one of said structures is different from the radius of gyration of other of said structures.

21. A mass accelerator according to claim 17 wherein the radius of gyration of said structures is the same for higher structures as for structures therebelow.

22. A mass accelerator according to claim 17 wherein the phase angle of gyrational movement of a structure is different from the phase angle of gyrational movement of an adjacent structure.

23. A mass accelerator according to claim 17 wherein the gyrational movement of each said structure is at (i) a gyration radius, (ii) a gyration frequency and (iii) a phase angle, at least one of (i), (ii) or (iii) being different for a structure than for an adjacent structure.

24. A mass accelerator according to claim 1 wherein at least one said arcuate surface has radii of increasing length from the upper most portion of its structure toward the adjacent lower structure.

25. A mass accelerator according to claim 1 wherein the arcuate surface of at least one of said structures includes means defining a pathway along which said projectiles move.

26. A mass accelerator according to claim 1 further including a control system for controlling one or more of the following functions:
   speed of movement of said structures,
   opening or closing of at least one said discharge outlet and starting or stopping said movement.

27. A mass accelerator according to claim 1 wherein said delay path includes a conduit having a first end connected to one structure, a second end connected to a second structure and tubing connected to said first and second ends, at least a portion of said tubing being flexible.

28. Apparatus for moving a mass comprising
(a) a first structure for receiving said mass, said first structure having a first internal surface upon which said mass can move, said first internal surface defining a first axis, said first structure bring gyratable;
(b) at least one second structure having an internal surface defining a second axis and having a second internal surface positioned to receive said mass from said first internal surface, said second structure being gyratable;
(c) first power means for imparting gyrational motion to said first structure to cause said first internal surface to gyrate; and
(d) second power means for imparting gyrational motion to said second structure to cause said second internal surface to gyrate; and
(e) a gap or delay length between said internal surface of said first structure for altering the path of movement of said mass as it moves from said first internal surface to said second internal surface in response to the gyrational movement of said first and second structures.

29. An apparatus for moving a mass according to claim 28 wherein said first and second axes are co-axial.

30. An apparatus for moving a mass according to claim 28 wherein said first axis is spaced from but parallel to said second axis.

31. Apparatus for moving a mass according to claim 28 wherein said first power means includes:
(f) a first primary driven gear,
(g) a first secondary gear rotatably engaged to said first primary driven gear, said first secondary gear being rotatable about an axis in reverse direction to said first primary driven gear and having a first gyrating pin spaced from said axis of rotation of said first secondary gear, said first gyrating pin attached to said first structure in an area to cause gyration of said first structure;
(h) a second primary driven gear; and
(i) a second secondary gear rotatably engaged to said second primary driven gear, said second secondary rotatable gear being rotatable about an axis in a reverse direction to said second primary driven gear and having a second gyrating pin spaced from said axis of rotation of said second secondary gear, said second gyrating pin attached to said second structure in an area to cause gyration of said second structure.

32. Apparatus for moving a mass according to claim 31 wherein the distance said first gyrating pin is spaced from the axis of rotation of said first secondary gear is the same as the distance said second gyrating pin is from the axis of rotation of said second secondary gear.

33. Apparatus for moving a mass according to claim 31 wherein the distance said first gyrating pin is spaced from the axis of rotation of said first secondary gear is different than the distance said second gyrating pin is from the axis of rotation of said second secondary gear.

34. Apparatus for moving a mass according to claim 31 wherein said first structure first internal structure is bowl shaped and has an outlet and said second structure has an inlet for receiving mass from said outlet and directing mass to said second internal surface.

35. Apparatus for moving a mass according to claim 31 wherein said second structure is positioned above said first structure and said second internal surface follows a path, in a plane passing through and perpendicular to said second axis, which is a member of the group consisting of (i) a straight line path extending upwardly in a direction away from said second axis, (ii) a straight line path parallel to said second axis, (iii) a straight line path extending upwardly in a direction toward said second axis and (iv) a curved path.

36. Apparatus for moving a mass according to claim 31 further including a lid on said second structure and an outlet in said second structure or said lid.

37. Apparatus for moving a mass according to claim 28 wherein the gyrational motion imparted to said second structure by said second power means is at a higher frequency than the gyrational motion of said first structure.

38. Apparatus for moving a mass according to claim 28 wherein the radius of gyration of said second structure is different than the radius of gyration of said first structure.

39. Apparatus for moving a mass according to claim 28 wherein said first internal surface is bowl-shaped and extends from a lower portion to an upper portion, said internal surface increasing in size in an upwardly direction.

40. Apparatus for moving a mass according to claim 39 wherein said second surface increases in size in an upwardly direction.

41. Apparatus for moving a mass according to claim 39 wherein said second internal surface is cylindrical.

42. Apparatus for moving a mass according to claim 28 further including one or more additional structures above said second structure each having an internal surface encircling an axis and positioned to receive said mass from the internal surface therebelow, each said additional structure connected to power means for imparting gyrational movement to cause each said additional structure internal surface to gyrate.

43. A method for moving a mass comprising the steps of:
(a) providing
(i) a first structure for receiving said mass, said first structure having a first internal surface upon which said mass can move, said first internal surface defining a first axis, and
(ii) at least one second structure having a second internal surface defining a second axis, said second internal surface positioned to receive said mass from said first internal surface,
(b) gyrating said first internal surface and said second internal surface to cause said mass to move on said first internal surface and thereafter on said second internal surface;
(c) creating a gap or delay length between said first internal surface and said second internal surface to alter the path of movement of said mass as it moves from said first internal surface to said second internal surface in response to the gyrational movement of said first and second internal surfaces.

44. A method for moving a mass according to claim 43 further including the step of aligning said first and second axes to be co-axial.

45. A method for moving a mass according to claim 43 further including the step of positioning said first and second internal surfaces such that said first axis is spaced from but parallel to said second axis.

46. A method for moving a mass according to claim 43 further including the steps of varying the frequency of gyration of said second internal surface from the frequency of gyration of said first internal surface.

47. A method for moving a mass according to claim 43 wherein each of said structures has a radius of gyration and further including the step of causing the radius of gyration of said first structure to be different from the radius of gyration of said second structure.

48. A method for moving a mass according to claim 43 where the gyration of each of said structures propelling said mass on their respective internal surfaces defines a phase angle and further including the step of varying the phase angle of at least one of said structures from the phase angle of at least one other of said structures.

49. A method for projecting a projectile comprising the steps of:
- (A) providing a mass accelerator for discharging said projectiles, said mass accelerator including:
  - (a) a plurality of structures each having an arcuate surface for supporting projectiles movable relative thereto, said structure being positioned one above the other from a lowermost structure to an uppermost structure, each said structure lying on an axis and being movable such that the portion of said arcuate surface on which a projectile is located moves substantially radially along a local radius of curvature;
  - (b) means for directing each projectile to the next adjacent arcuate surface upon reaching the upper area of said arcuate surface for that structure; and
  - (c) a discharge outlet on the uppermost of said structures;
- (B) introducing said projectiles into contact with the arcuate surface of said lowermost structure;
- (C) moving each arcuate surface substantially radially along a local radius of curvature perpendicular to its axis when said projectile is located on said arcuate surface;
- (D) directing said projectiles to the arcuate surface of the adjacent higher structure; and
- (E) discharging said projectiles from the uppermost structure.

50. A method for accelerating movement of a mass moving along a pathway of a structure, said structure having an inlet leading to said pathway and an outlet from said pathway, said pathway following a first directional course in the area adjacent and said inlet, comprising the steps of;
- (a) gyrating said structure to move said structure along a local radius of curvature to induce movement of said mass in said pathway; and
- (b) providing (i) a delay length or (ii) a gap in said pathway to alter said directional course of said mass.

51. A method for accelerating movement of a mass according to claim 50 further including the step of enlarging the system diameter in the area of said pathway leading toward said outlet.

52. A method for accelerating movement of a mass according to claim 50 further including the step of reducing the system diameter in the area of said pathway leading toward said outlet.

* * * * *